(12) United States Patent
Schöb et al.

(10) Patent No.: US 6,670,169 B1
(45) Date of Patent: Dec. 30, 2003

(54) BIOREACTOR

(75) Inventors: Reto Schöb, Volketswil (CH); Jörg Hugel, Zürich (CH)

(73) Assignee: Levitronix LLC, Waltham, MA (US)

( * ) Notice: Subject to any disclaimer, the term of this patent is extended or adjusted under 35 U.S.C. 154(b) by 0 days.

(21) Appl. No.: 09/655,204

(22) Filed: Sep. 5, 2000

(30) Foreign Application Priority Data

Sep. 8, 1999 (EP) .............................................. 99810806
Aug. 18, 2000 (EP) .............................................. 00810733

(51) Int. Cl.⁷ .............................................. C12M 1/36
(52) U.S. Cl. .............................. 435/286.5; 435/286.7; 435/289.1; 435/293.1; 435/295.2; 417/360; 623/3.13
(58) Field of Search .......................... 435/289.1, 286.5, 435/286.1, 286.7, 293.1, 295.1, 295.2; 417/360; 600/16, 17; 623/3.1, 3.13; 604/131, 151

(56) References Cited

U.S. PATENT DOCUMENTS

| | | | | | |
|---|---|---|---|---|---|
| 3,460,810 A | * | 8/1969 | Mueller | .................. | 366/263 |
| 3,536,305 A | * | 10/1970 | Lefrancois | .................. | 261/93 |
| 3,635,796 A | * | 1/1972 | Imada et al. | .................. | 435/3 |
| 3,873,423 A | * | 3/1975 | Munder et al. | .................. | 435/3 |
| 3,957,585 A | * | 5/1976 | Malick | .................. | 435/246 |
| 4,001,090 A | * | 1/1977 | Kalina | .................. | 435/243 |
| 4,519,959 A | * | 5/1985 | Takeuchi et al. | .................. | 261/93 |
| 4,684,614 A | * | 8/1987 | Krovak et al. | .................. | 435/295.1 |
| 4,889,812 A | * | 12/1989 | Guinn et al. | .................. | 435/289 |
| 5,205,819 A | * | 4/1993 | Ross et al. | .................. | 604/67 |
| 5,593,890 A | * | 1/1997 | Flores-Cotera et al. | .. | 435/286.5 |
| 5,614,412 A | * | 3/1997 | Smith et al. | .................. | 435/305.1 |
| 6,071,093 A | * | 6/2000 | Hart | .................. | 417/424.2 |
| 6,210,133 B1 | * | 4/2001 | Aboul-hosn et al. | ..... | 417/423.1 |
| 6,391,638 B1 | * | 5/2002 | Shaaltiel | .................. | 435/383 |

* cited by examiner

*Primary Examiner*—David A. Redding
(74) *Attorney, Agent, or Firm*—Towsend and Townsend and Crew, LLP

(57) ABSTRACT

A bioreactor with a reaction container (1, 1a, 1b, 1c) for a substance (C) to be acted upon with a medium has a pump (5, 5a, 5b, 5c, 5d) for conveying the medium. The pump is designed as an expendable pump or, respectively, parts (53d, 54d, 55d) of the pump are designed as expendable parts.

17 Claims, 18 Drawing Sheets

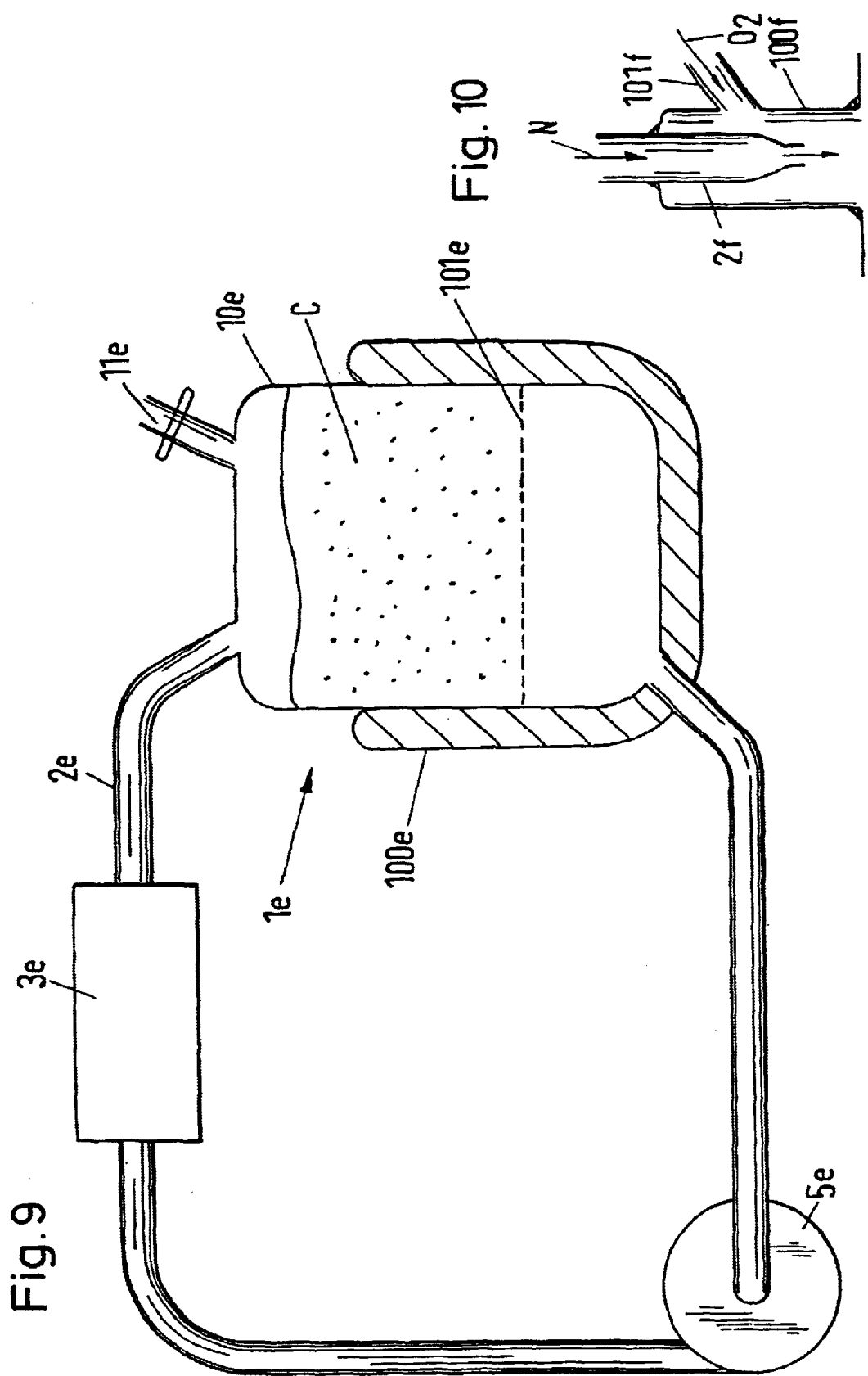

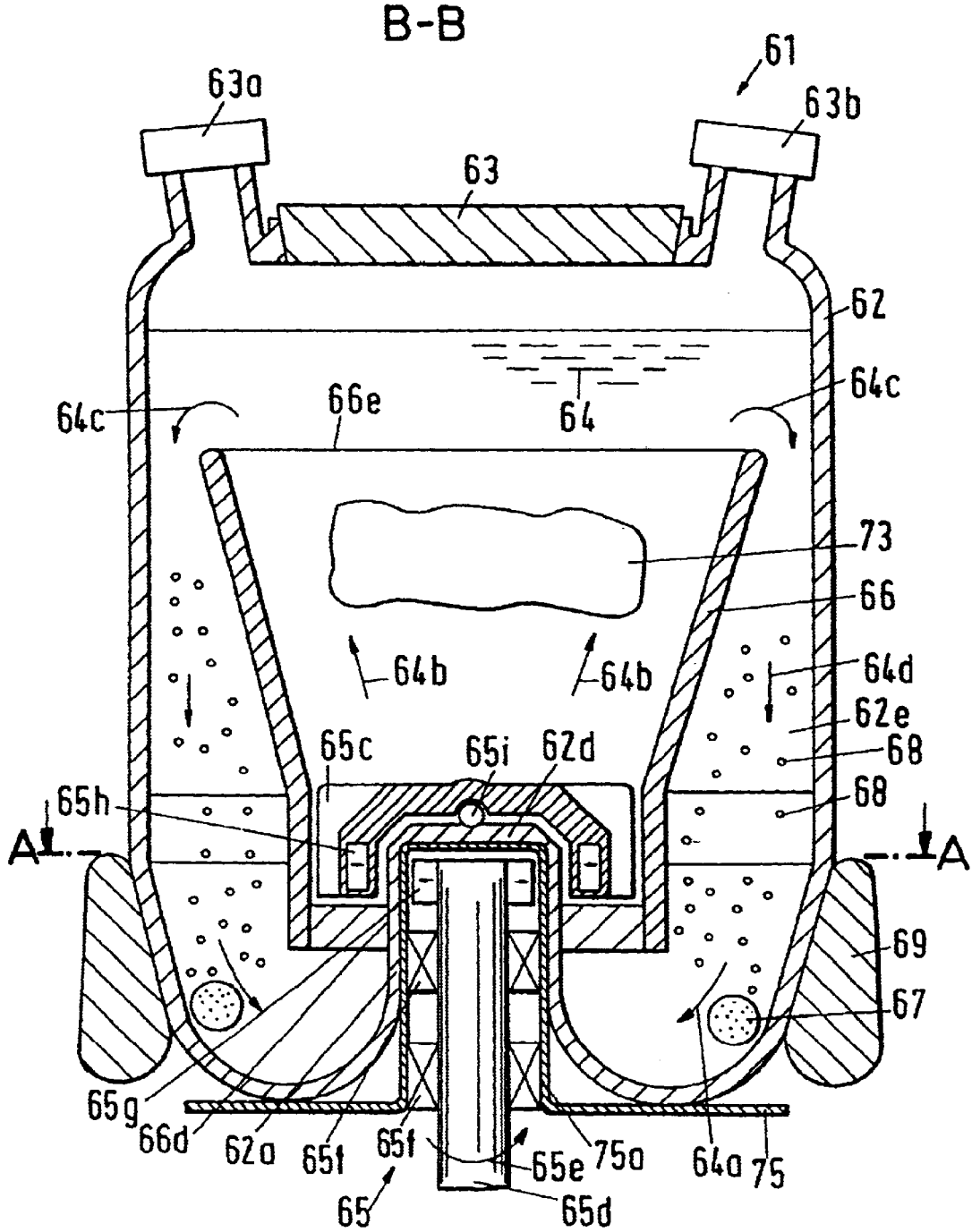

A-A

BIOREACTOR

BACKGROUND OF THE INVENTION

The invention relates to a bioreactor which has a reaction container for a substance to be acted upon with a medium and a pump for conveying the medium.

Nowadays one frequently speaks of bioreactors when one speaks about the field of "tissue engineering". A prominent goal in this field is to produce biological substitutes for damaged tissue or organs. But there is still a large number of other goal fields; for example the effectivity or toxicity of pharmaceutica can be tested using tissue of this kind, which can eliminate the future need for a large number of animal experiments and/or clinical experiments on humans.

Bioreactors are used in the production of tissue of this kind. In this the most diverse of reactor types are used, such as for example the so-called hollow fiber reactors. A hollow fiber reactor of this kind is known for example from U.S. Pat. No. 5,622,857. This reactor comprises a reaction container, through which a central strand of porous hollow fibers extends, through which a nutrient solution is pumped. This central strand of hollow fibers is concentrically surrounded by a plurality of strands of hollow fibers, through which a gaseous medium is conveyed. The hollow fibers of these strands are also constituted in such a manner that the gaseous medium—for example oxygen or carbon dioxide—can at least partly emerge from these strands or enter into these strands respectively.

A cavity is in each case formed, both between the central strand and the strands surrounding this central strand as well as between these strands surrounding the central strand and the container wall. There the substance—e.g. parent cells or whatever—which is to be acted upon with the various media can be made available, where appropriate on a so-called "micro-carrier" or a biodegradable matrix material. The nourishing of the substance takes place through the liquid nutrient solution, which can emerge to a certain extent from the pores of the central strand, and its provision with oxygen takes place through the gaseous medium.

Since as a rule the nutrient solution which again emerges from the reaction container is recirculated and used again for the next run, supplemented where appropriate by further nutrient solution, a "contamination" can of course easily occur. This is important insofar as these parts must be very intensively sterilized for the tissue of another patient in order that a contamination cannot arise. In spite of any sterilization of the individual parts, however intensive, a hundred percent sterilization cannot always be ensured. The sterility is however of central importance for the success of the "tissue engineering".

For the reaction container and for the supply lines a new reaction container and new supply lines respectively are already used in every employment.

But the pump can also be contaminated in employments of this kind. Since considered from the point of view of expenditure, the pumps are devices which still involve great expense, the latter are sterilized with a relatively great expenditure.

SUMMARY OF THE INVENTION

The present invention is dedicated to this disadvantage. An object of the invention is to propose a bioreactor in which the sterility can be ensured with great reliability in order not to endanger from the beginning the success of a "tissue engineering" process which is to be carried out with this reactor for lack of sterility; on the other hand the expenditure for this should be as low as possible.

This object is satisfied in accordance with the invention by providing the bioreactor with an expendable pump.

In particular the pump for the conveying of the medium and/or, respectively, parts of the pump are designed as expendable or disposable parts. Through this the sterilization of the pump involving great expense is omitted.

In an advantageous exemplary embodiment the expendable parts of the expendable pump are manufactured of a plastic, since parts of this kind can be economically manufactured with great reliability, for example through injection molding processes.

In a further advantageous exemplary embodiment the expendable pump comprises a pump housing in which the pump wheel is arranged as well as a separate drive stator into which the pump housing together with the pump wheel which is arranged therein can be inserted. In this the housing together with the pump wheel which is arranged therein is designed as an expendable part. This exemplary embodiment is particularly advantageous insofar as all "contaminatable parts", namely the pump housing (inner wall) and the pump wheel which is arranged therein, can be replaced after every employment in the simplest manner, and the complicated and expensive parts (electrical supply of the drive, etc.) can be maintained and reused for the next employment without any danger of contamination existing. Furthermore, the electrical drive represents the most complicated and expensive part of the pump not only from the technical, but also from the economical point of view. The latter need however not be replaced, but rather only the less complicated and expensive pump housing with the pump wheel which is arranged therein.

In an advantageous further development of this exemplary embodiment permanent magnets are arranged in the pump wheel which then, together with the electromagnetic field which is produced by the drive stator, drive the pump wheel.

In an advantageous manner the expendable pump can be designed as a gear pump. This is a constructionally particularly simple type of pump which is also very economical to manufacture. Furthermore, gear pumps do not display the fatigue phenomena such as for example squeezed tube pumps, which are otherwise frequently used in such applications.

The bioreactor can for example be designed as a hollow fiber bioreactor, as has already been explained initially with reference to a special exemplary embodiment.

The bioreactor can however also be designed as a so-called airlift reactor ("Blasenreaktor"). In an airlift reactor it is in principle a matter of carrying out the liquid supplying (nutrient solution) and the likewise required supplying with gases such as e.g. oxygen in such a manner that bubbles rise in the liquid or are held there in flotation respectively.

In an exemplary embodiment of an airlift reactor of this kind the latter comprises a reaction container in which a hollow body is arranged, of which the jacket is connected at its lower end to the wall of the reaction container and tapers in the direction towards the upper end of the reaction container so that it subdivides the inner space of the reaction container into an upper chamber and a lower chamber. The upper and lower end side of the hollow body are designed to be liquid and gas permeable (e.g. as membrane) and enclose a cavity in which the substance to be acted upon (e.g. the cells or the micro carrier with the cells or the biodegradable matrix material with the cells) can be arranged. Depending on the kind of the employment however one or both membranes need not necessarily be present. The supply line for the liquid medium opens into the upper chamber and a suction device for the liquid medium is provided in the lower chamber. Through this a liquid flow is produced which comes from above and passes through the cavity in which the substance to be acted upon is arranged and into the lower chamber. A supply device for the gaseous medium is arranged in the lower chamber. This has the effect that the bubbles rise in the liquid. Since the speed of the liquid flow in the upper region of the cavity is however greater (smaller diameter) than in the lower region (greater diameter) the rising bubbles in the upper region are again taken along by the flow downwards where the flow speed of the liquid flow is again lower, for which reason the bubbles again begin to rise. Through a corresponding choice of the flow speed it is thus possible to "concentrate" the bubbles in the cavity in which the substance to be acted upon is arranged.

In a further development of an airlift reactor of this kind the reaction container is designed to be cylindrical and the hollow body is designed to have the shape of a truncated circular cone. In this the supply line opens into a preferably ring-shaped or circular areal distributor which is arranged in the upper chamber and surrounds the hollow body. The suction device for the liquid medium, which is arranged in the lower chamber, is likewise preferably designed to be ring-shaped or circularly areal. This yields on the one hand a well controllable flow and ensures on the other hand that the distributor as well as the suction device can also be used when the dimensions of the container and the hollow body which is arranged therein should happen not to correspond so precisely to the desired dimensions.

In a further exemplary embodiment of the airlift reactor the latter comprises a reaction container in which a hollow body is arranged, of which the jacket is connected at its upper end to the wall of the reaction container and which tapers in the direction towards the lower end of the reaction container so that it subdivides the inner space of the reaction container into an upper chamber and a lower chamber. The upper and lower end surface of the hollow body are in each case designed to be liquid and gas permeable (e.g. as a membrane or as a net or as a filter mat) and enclose a cavity in which the substance to be acted upon can be arranged. The supply line for the medium opens here into the lower chamber, with the gaseous medium already being admixed to the liquid medium (e.g. by means of an oxygenator). A suction device for the medium through which a desired flow speed can be produced is provided in the upper chamber. The flow speed is directed upwards, with it being the greatest in the lower region of the hollow body and decreasing upwardly through the widening of the hollow body. Through this the cells which are located between the two membranes are held in flotation, through which good conditions for the growth of a three-dimensional cell compound (tissue) result.

In another exemplary embodiment the reaction container can comprise a flexible pouch which can be inserted into a dimensionally stable reception. This reception can for example be designed as a thermal jacket and hold the temperature of the medium at a desired temperature. In addition the thermal jacket lends the required stability to the flexible pouch.

Finally, in all exemplary embodiments not only the pump and/or parts thereof are designed as expendable parts. In addition, all other constituents of the bioreactor which come into contact with the medium can also be designed as expendable parts. The bioreactor can thus already be delivered as an assembled bioreactor packed in a sterile condition which is replaced after each employment.

The essential idea of the invention is thus the use of an expendable pump or a pump with parts which are designed as expendable parts in a bioreactor, which however, as explained above, can be realized in many different manners. However, a bioreactor can also be used in an advantageous manner in which all parts which come into contact with the medium are designed as expendable parts. In this way a contamination in a second employment (which thus does not exist with the same bioreactor) is reliably avoided.

The artificial production of tissue material, often called "tissue engineering", is increasingly gaining in importance in order to produce biological substitutes for damaged tissue or damaged organs. Artificial tissue material can be produced in that cell cultures in vitro are deposited at or in a tissue carrier, also designated as a matrix. The tissue carrier consists for example of a synthetic polymer or of a biological material such as collagen. A tissue carrier of this kind is also designated as a "scaffold". The cells are sown out onto the tissue carrier and begin to multiply if the environmental parameters are physiologically favorable. The tissue carrier can be designed in such a manner that the latter disintegrates with time, so that after a certain time only the tissue part which is formed from the cells is present. The tissue carrier and/or the tissue part which is formed on it is designated as "substance" in the following. The conditions which are required for the cell growth are produced in a bioreactor, within which the required oxygen and a nutrient medium are supplied to the substance and within which the substance remains from several days to weeks until the desired size has been reached. The geometrical shape which the artificially produced tissue material assumes during growth is substantially influenced through the measures by means of which the substance is held in the bioreactor.

Thus in the following the term "substance" will be understood to mean both the tissue carrier per se and the tissue carrier with cells deposited on it, or, if the tissue carrier is designed to be decomposable, the artificially produced cell culture or the artificially produced tissue part respectively.

As a method for the holding in flotation of a substance in a bioreactor the substance is preferably acted upon with a fluid, with the flow of the fluid acting counter to gravitation in such a manner that the substance is held in flotation.

This method has the advantage that the substance is held without contact in the bioreactor in that the fluid, usually a liquid, has a flow which is developed in such a manner that the substance is held without contact by the flow, which acts counter to gravitation. In this the substance is usually also kept continually in motion so that its position changes continually. This method has the advantage that the cells grow uniformly at or in the substance respectively and the growth of the substance is favored. Disadvantageous in the previously known methods for the artificial production of tissue is the fact that it had been possible to produce only flat, substantially two-dimensional structures.

In a particularly advantageously designed method the fluid has an increasingly lower flow speed in the direction opposite to gravitation. This flow behavior is for example produced in that the flowing fluid is led from below into a hollow body having the shape of a truncated cone which widens upwardly. The cross-section of the hollow body, which widens upwardly, causes the flow speed in the hollow body to be reduced with increasing height. The substance is continually held in flotation in the inner space of the hollow body, with the side walls of the hollow body limiting a lateral movement of the substance, so that the substance is always located in the upwardly flowing liquid. With increasing cellular growth the weight of the substance increases, so that the substance moves slightly downwards in the inner space of the hollow body and finds again a new equilibrium position there. The substance thus automatically seeks the respective equilibrium position. It can however prove advantageous to monitor the position of the substance with a sensor and to influence the speed of the upwardly flowing fluid by means of the measured signal. Thus the speed of the fluid can for example be regulated in such a manner that the substance is continually held in flotation in a predetermined position.

In an advantageous method, in addition to the upward flow within the bioreactor a downward flow is also produced, with a gaseous fluid such as air or oxygen being supplied to the downwardly flowing fluid, usually a liquid. The speed of the downwardly flowing fluid is advantageously chosen such that the gaseous fluid which is input is slowed down or no longer rises at all, so that the gaseous fluid remains relatively long in the flowing fluid and can be taken up or absorbed respectively by the latter.

An advantageously designed bioreactor comprises a container for a substance which is to be acted upon with a fluid, with the container comprising a first flow chamber to which a flowing fluid can be supplied, and with the first flow chamber being designed in such a manner that the fluid which flows upwardly therein has a lower speed with increasing height. In a particularly advantageous embodiment the flow chamber has an upwardly widening cross-section.

In a further advantageous design a flow guiding means is arranged within the bioreactor and forms a flow chamber which widens upwardly. This flow guiding means preferably forms in addition within the bioreactor a further, second flow chamber which widens downwardly and into which a gaseous fluid can be led.

In a further, advantageous embodiment a drivable pump wheel is arranged within the bioreactor, with the help of which the flow of the fluid within the bioreactor can be produced. The pump wheel is advantageously magnetically coupled to a drive which is arranged outside the housing of the bioreactor. The bioreactor housing and the pump wheel are advantageously conceived as throw-away or expendable products respectively so that the latter can be disposed of after a single use. These parts can be manufactured economically. For example the pump wheel can comprise a vaned wheel of plastic into which a permanent magnet is cast. All expensive components such as the drive apparatus are arranged outside the bioreactor. The design of the bioreactor as an expendable product has the advantage that no laborious cleaning process is required and that a contamination of the artificially produced tissue material is largely excluded. The avoiding of a contamination is of decisive importance since the substance remains for example four to eight weeks in the bioreactor, until sufficient artificial tissue material has been formed. Since the bioreactor has no immune reaction system, the slightest contaminations such as bacteria, fungi or viruses can already result in the produced artificial tissue dying off or being contaminated. Through the design of the bioreactor as an expendable product, artificial tissue material can be economically and reliably produced.

BRIEF DESCRIPTION OF THE DRAWINGS

FIG. 9 shows a further exemplary embodiment of a bioreactor made in accordance with the invention which is provided with a flexible pouch;

FIG. 10 shows an exemplary embodiment of how the inlet into the reaction container can be designed in order to replace an oxygenator;

FIGS. 12a, 12b are longitudinal sections through further exemplary embodiments of bioreactors;

FIGS. 13a–13d are longitudinal sections through further exemplary embodiments of bioreactors;

FIG. 14 is a longitudinal section along line B—B through a further bioreactor with a magnetically coupled vaned wheel;

DESCRIPTION OF THE PREFERRED EMBODIMENTS

Figure 1:
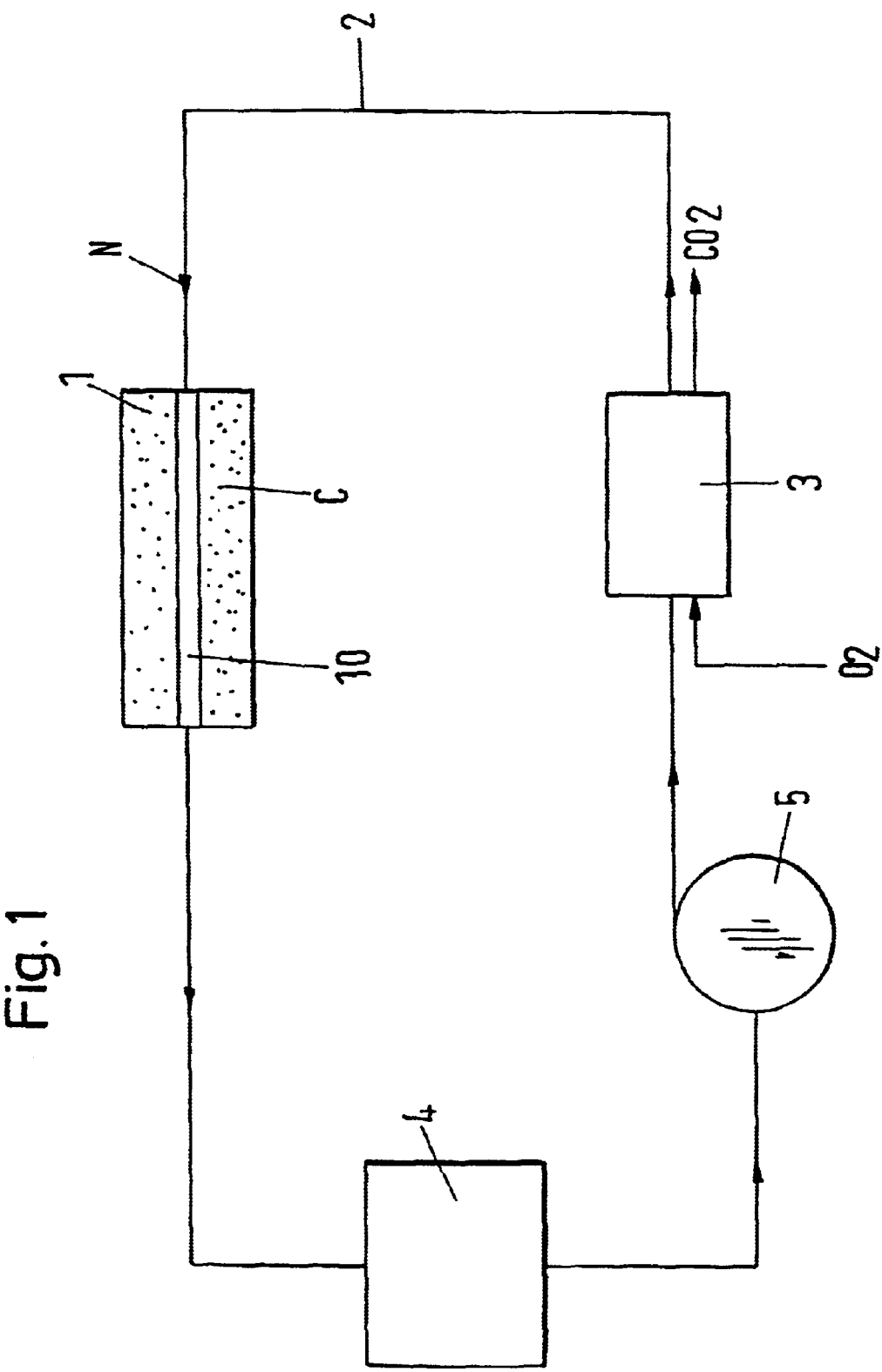
FIG. 1 shows an exemplary embodiment of a bioreactor made in accordance with the invention which is designed as a hollow fiber reactor.

A first exemplary embodiment of a bioreactor in accordance with the invention is illustrated in FIG. 1. One recognizes a reaction container 1, which is designed here as a hollow fiber reactor. In the inner space of the reaction container hollow fibers are or a bundle 10 of hollow fibers respectively is arranged and through which a liquid medium flows, for example a nutrient solution N which is supplied through a supply line 2. Cells C can be arranged in the reaction container 1 and can be supplied with nutrients with the help of the nutrient solution N. A gas, for example oxygen, which was added to the nutrient solution N in an oxygenator 3 and which can likewise serve for supplying the cells C, can be contained in the nutrient solution N. The hollow fibers of the hollow fiber bundle 10 are porous, so that the gas and the nutrients or the nutrient solution respectively can reach the cells C in the reaction container 1.

The nutrient solution N which flows out of the reaction container 1 can flow through a reservoir 4 where it is renewed or enriched again with nutrients respectively. The nutrient solution N is pumped with the help of a pump 5 out of the reservoir through the oxygenator 3, where e.g. oxygen is added to or carbon dioxide is removed from the nutrient solution. This pump 5 is now designed in accordance with the invention as an expendable pump or throw-away pump. It is preferably manufactured of a plastic such as for example polycarbonate or polyvinylchloride (PVC) and can be manufactured for example by injection molding. This expendable pump or throw-away pump 5, or the "contaminated" parts thereof respectively, are replaced after every use, so that no danger of contamination can even exist for the subsequent use. The expendable pump 5 or, respectively, those parts of it which are designed as expendable parts and are replaced are delivered in sterile packings and are preferably designated in such a manner that they indicate to the user that the pump or the parts thereof respectively are intended to be used only once. In this the expendable pump 5 can advantageously be designed as a gear pump, as will be described more precisely in the following. These gear pumps involve low expense in their construction and therefore in their manufacturing and moreover do not display the disadvantageous fatigue phenomena of squeezed tube pumps, which are otherwise frequently used in employments of this kind.

Figure 2:
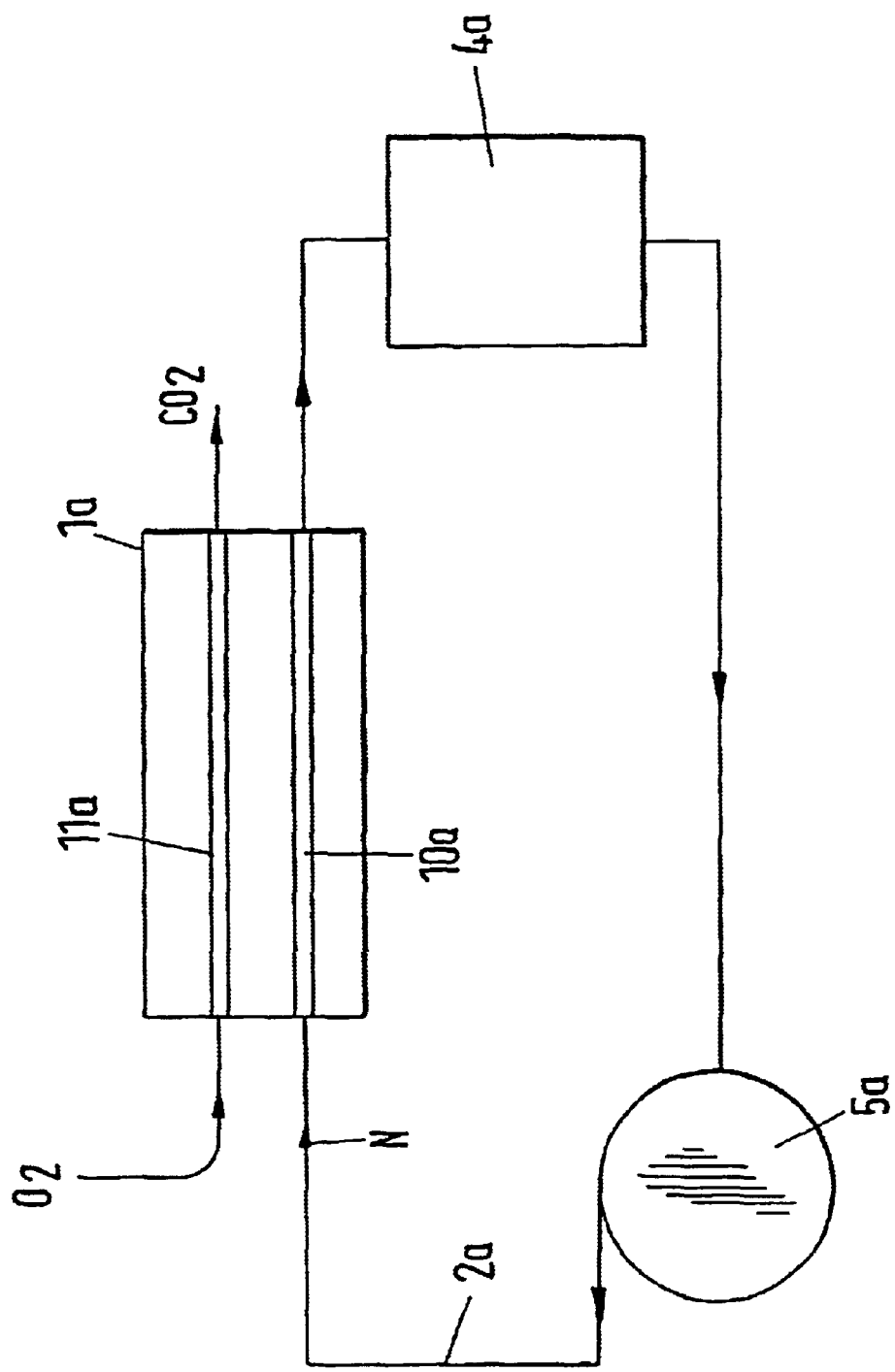
FIG. 2 shows a further exemplary embodiment of a bioreactor made in accordance with the invention which is designed as a hollow fiber reactor.

In FIG. 2 a further exemplary embodiment of a hollow fiber reactor is illustrated. The reaction container 1a in this exemplary embodiment has two hollow fiber bundles 10a and 11a in its inner space, with the hollow fiber bundle 10a having the same function as in the exemplary embodiment in accordance with FIG. 1. Namely, through this bundle 10a the nutrient solution N flows, which supplies the cells C which are located in the reaction container 1a with nutrients. The supply of oxygen or the removal of carbon dioxide takes place however in this exemplary embodiment—in contrast to the exemplary embodiment of FIG. 1—through the hollow fiber bundle 11a, which is likewise arranged in the reaction container 1a. Thus the supplying of the cells C with gases such as e.g. oxygen takes place in a manner which is decoupled and separate from the nutrient supply. The nutrient solution N which flows out of the reaction container 1a flows through a reservoir 4a again in which the nutrient solution can be renewed or again enriched with nutrients before it is supplied anew to the reaction container. The pumping of the nutrient solution is effected with the help of the expendable pump or throw-away pump 5a, which is designed completely analogously to the pump which was already briefly explained with reference to FIG. 1. It can for example also be designed as a centrifugal pump however.

Figure 3:
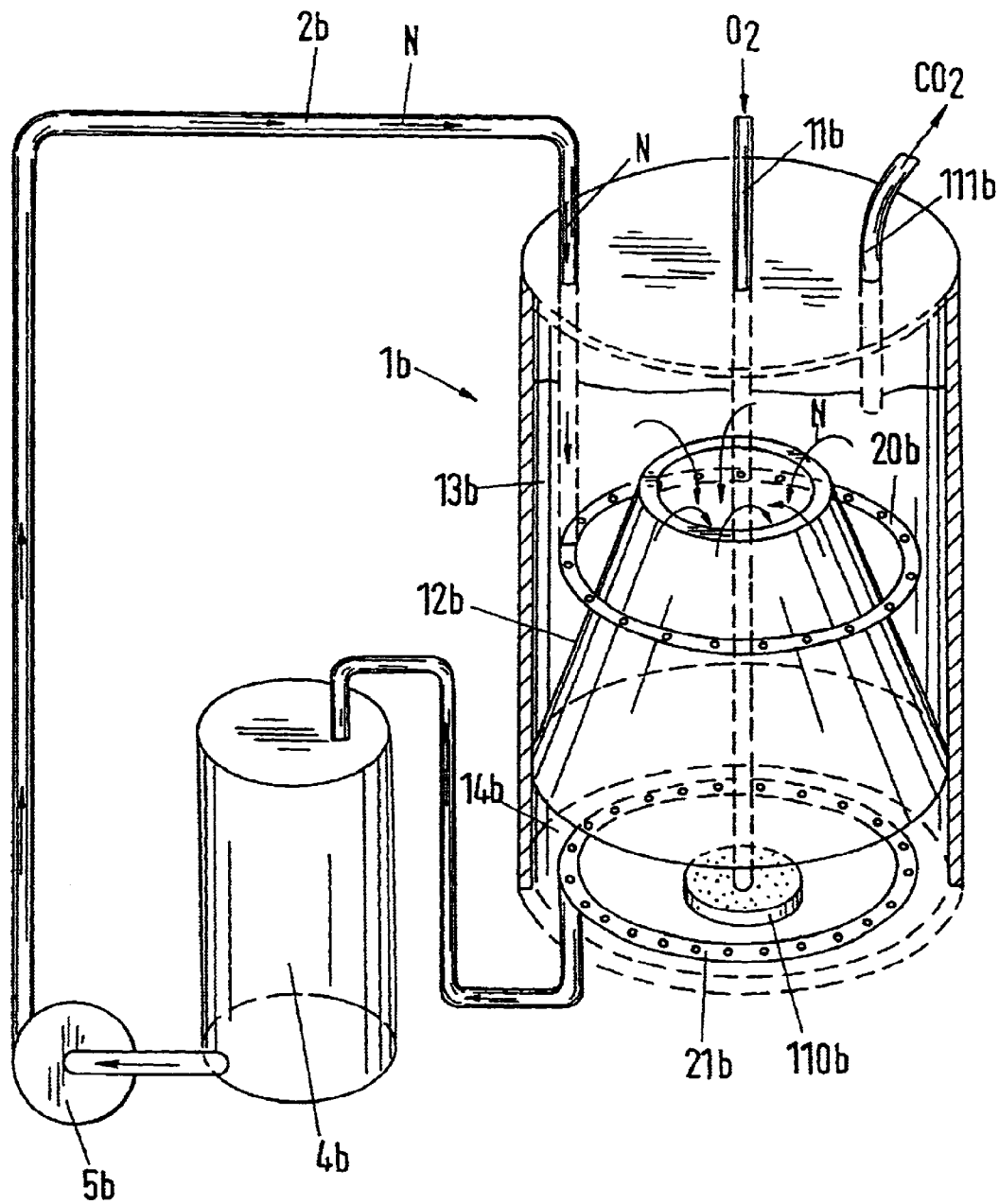
FIG. 3 shows an exemplary embodiment of a bioreactor made in accordance with the invention which is designed as an airlift reactor.

A further exemplary embodiment of a bioreactor which is designed as an airlift reactor is illustrated in FIG. 3. One recognizes the reaction container 1b, in which a hollow body 12b in the shape of a truncated circular cone is arranged. At its lower end the hollow body 12b is connected to the wall of the reaction container 1b. From there the hollow body 12b tapers upwardly so that it subdivides the inner space of the reaction container into an upper chamber 13b and a lower chamber 14b. The upper and lower end surfaces of the hollow body 12b are designed to be gas and liquid permeable, which cannot be recognized in FIG. 3, but in FIG. 4 however. There it can be seen that in the region of the upper and lower end surface in each case a membrane 15b and 16b respectively is arranged which is gas and liquid permeable. Thus the two membranes enclose a cavity in which the cells C are arranged, for which however the membranes are impermeable. Depending on the employment, however, one or both membranes may be absent.

Furthermore, one also recognizes the supply line 2b for the nutrient solution N, which leads to a ring-shaped distributor 20b which is arranged in the upper chamber 13b and surrounds the hollow body 12b. A suction device 21b which is likewise designed to be ring-shaped and which is connected to a removal line which leads to the reservoir 4b is provided in the lower chamber 14b. There the nutrient solution N is renewed or enriched with nutrients respectively. Thus the expendable pump 5b is provided for the conveying of the nutrient solution, which was already mentioned. The nutrient solution N is thus conducted with the help of the expendable pump 5b out of the reservoir 4b through the supply line 2b into the ring-shaped distributor 20b; from there it flows through the membrane 15b and through the cavity of the hollow body 12b. Then the nutrient solution flows through the membrane 16b and is sucked off by the suction device 21b and conveyed back into the reservoir 4b, through which the nutrient solution circuit is closed.

As far as the supplying of the cells C with gases, e.g. with oxygen, is concerned, these are conducted through the line 11b to a distributor 110b which is arranged in the lower chamber 14b. There the gases emerge from the distributor 110b in the form of bubbles and rise. The liquid flow, which is of course directed downwards, acts counter to this rising of the bubbles. Through suitable choice of the flow parameters it can be achieved that the bubbles have a sufficiently long dwell time in the cavity, where the cells C are arranged (and which is surrounded by the hollow body 12b). A corresponding removal line 111b is provided for the emerging gases.

Figure 4:
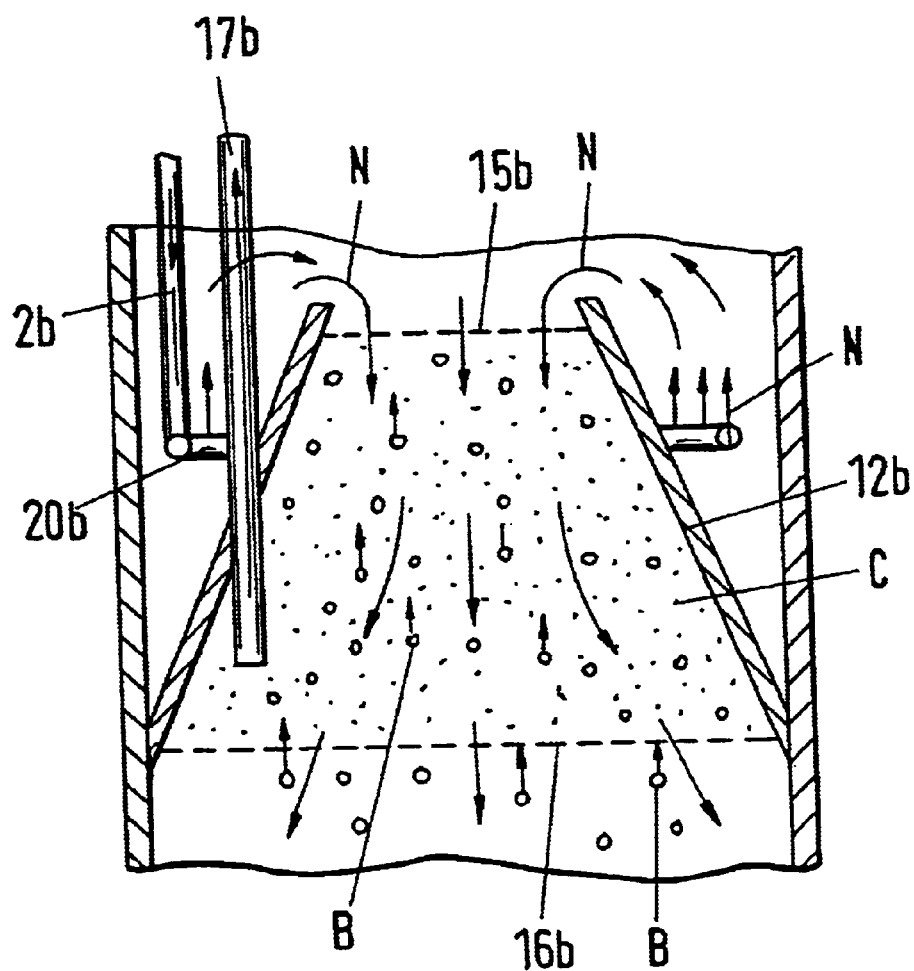
FIG. 4 is an enlarged section of the airlift reactor of FIG. 3.

If now the desired cells C or e.g. a piece of tissue are correspondingly matured and one wishes to take out cells C or a piece of tissue, then this can take place through a so-called "harvesting" channel 17b, as is indicated in FIG. 4. There one also recognizes particularly well the direction of the flow of the nutrient solution N, the direction of the rising gas bubbles B, which extends counter to this flow, and the cells C which are enclosed by the hollow body 12b and the membranes 15b and 16b.

Figure 5:
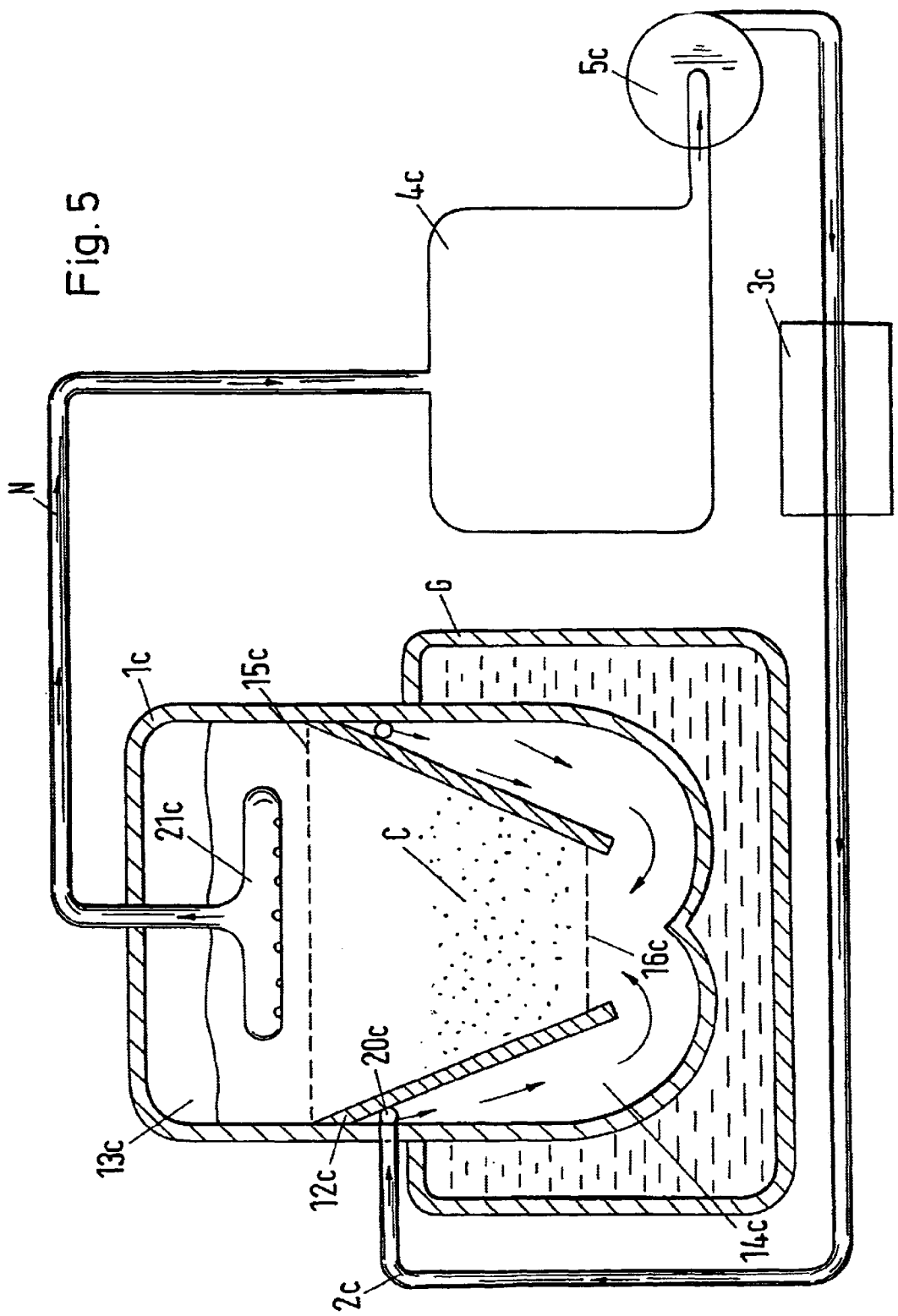
FIG. 5 shows a further exemplary embodiment of a bioreactor which is designed as an airlift reactor.

A further exemplary embodiment of a bioreactor in which cells are cultivated is illustrated in FIG. 5. One recognizes the reaction container 1c, which is surrounded here by a further vessel G in which for example water can be contained in order for example to be able to hold the reaction container 1c at a desired temperature. A hollow body 12c in the shape of a truncated circular cone which subdivides the container 1c into an upper chamber 13c and a lower chamber 14c is arranged in the reaction container. The jacket of the hollow body 12c, which is in the shape of a truncated circular cone, is connected at its upper end to the wall of the reaction container 1c and tapers in the direction towards the lower end of the reaction container. The upper and lower end surface of the hollow body 12c are designed to be gas and liquid permeable, and indeed in such a manner that in the region of the upper and lower end surface in each case a membrane 15c and 16c is respectively arranged which is designed to be gas and liquid permeable. Cell carriers, for example consisting of plastic or ceramics, with cells C, for which the membranes 15c and 16c are impermeable, can be arranged in the cavity, which is enclosed between the membranes 15c and 16c. The supply line 2c for the nutrient solution N opens in the lower chamber 14c into a ring-shaped distributor 20c which surrounds the hollow body 12c. A suction device 21c is provided in the upper chamber 13c and is connected to a removal line which leads to the reservoir 4c, where the removed nutrient solution N can be renewed or enriched with nutrients respectively. For the conveying of the nutrient solution N an expendable pump 5c or a pump with expendable parts respectively is provided which—as already explained above—can for example be designed as a gear pump or as a centrifugal pump.

The nutrient solution N, which is conveyed by the pump 5c out of the reservoir 4c, enters into an oxygenator 3c, where a gas such as for example oxygen can be admixed to or carbon dioxide can be removed from the nutrient solution N. The nutrient solution N, which is thus mixed with oxygen or freed from carbon dioxide respectively, then enters later on into the ring-shaped distributor 20c, which is arranged in the lower chamber 14c. With the help of the expendable pump 5c and the suction device 21c a liquid flow is produced which is indicated by the arrows in FIG. 5. In the region of the membrane 16c the flow speed is comparatively high—it then decreases as a result of the hollow body 12c, which widens in the manner of a truncated cone. Through a suitable choice of the flow parameters it can be achieved that the cells C are held in flotation in the region between the membranes 16c and 15c. This can favor the formation of a three-dimensional cell compound (tissue). In this exemplary embodiment the supplying of nutrient solution N on the one hand and of gases such as e.g. oxygen on the other hand do not take place separately, but rather the nutrient solution N is mixed with oxygen before it is introduced with the help of the supply line 2c and the distributor 20c into the container 1c.

Figure 6:
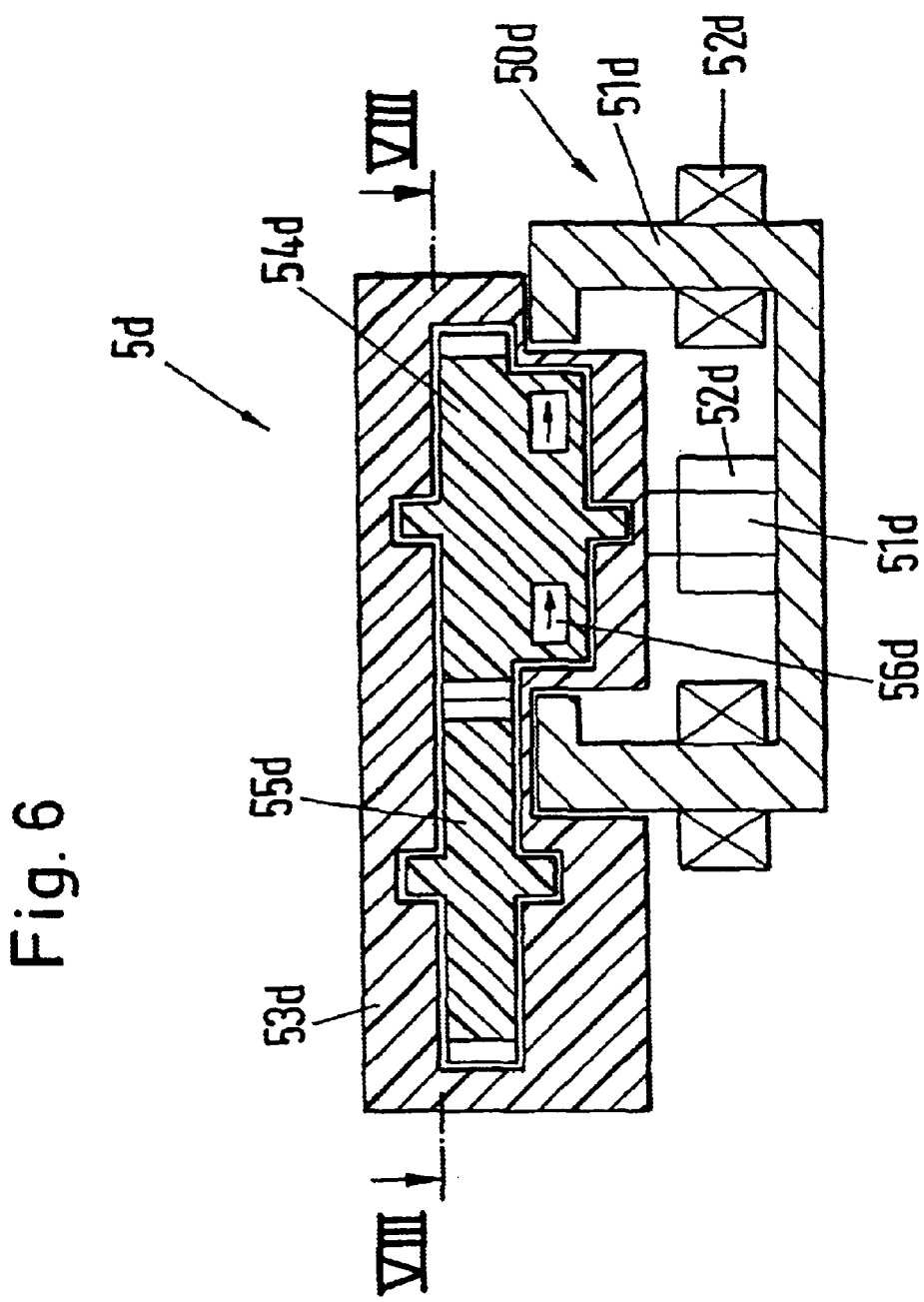
FIG. 6 shows an exemplary embodiment of an expendable pump in the form of a gear pump which can be used in a bioreactor.

In FIG. 6 an exemplary embodiment for the expendable pump which was already mentioned above is shown. This exemplary embodiment of the expendable pump is designed as a gear pump 5d. One recognizes the stator 50d with the stator limbs 51d (three stator limbs can be recognized in FIG. 6), around which the drive windings 52d are wound. Furthermore, one recognizes a pump housing 53d which is manufactured of an injection moldable plastic, for example of polycarbonate or polyvinylchloride (PVC). The same holds for the two gears 54d and 55d which are arranged in the pump housing 53d, with it being possible for permanent magnets 56d to be injection molded in the drive gear 54d. All parts which are arranged in the pump housing 53d, thus both gears 54d and 55d as well as the pump housing 53d itself, are thus manufactured here of an economical injection moldable plastic, which is simple to deal with with regard to the manufacture. This has the consequence that it is easily defensible to replace the pump housing 53d with the gears 54d and 55d which are located therein after every employment. A laborious and furthermore not absolutely reliable sterilization of the pump 5d, which includes the danger of a contamination, can thereby be avoided.

It can likewise easily be seen in FIG. 6 that the expense for replacing the pump housing 53d is extremely low. For this purpose the pump housing need merely be taken out of the stator 50d upwardly and a new (sterile and thus not contaminated) pump housing 53d then inserted again from above. A plan view from above onto a stator 50d of this kind with its stator limbs 51d and the drive windings 52d which are wound around these stator limbs 51d can be seen in FIG. 6. This plan view once again clarifies that the replacing of the pump housing is possible rapidly and reliably and practically without effort.

Figure 8:
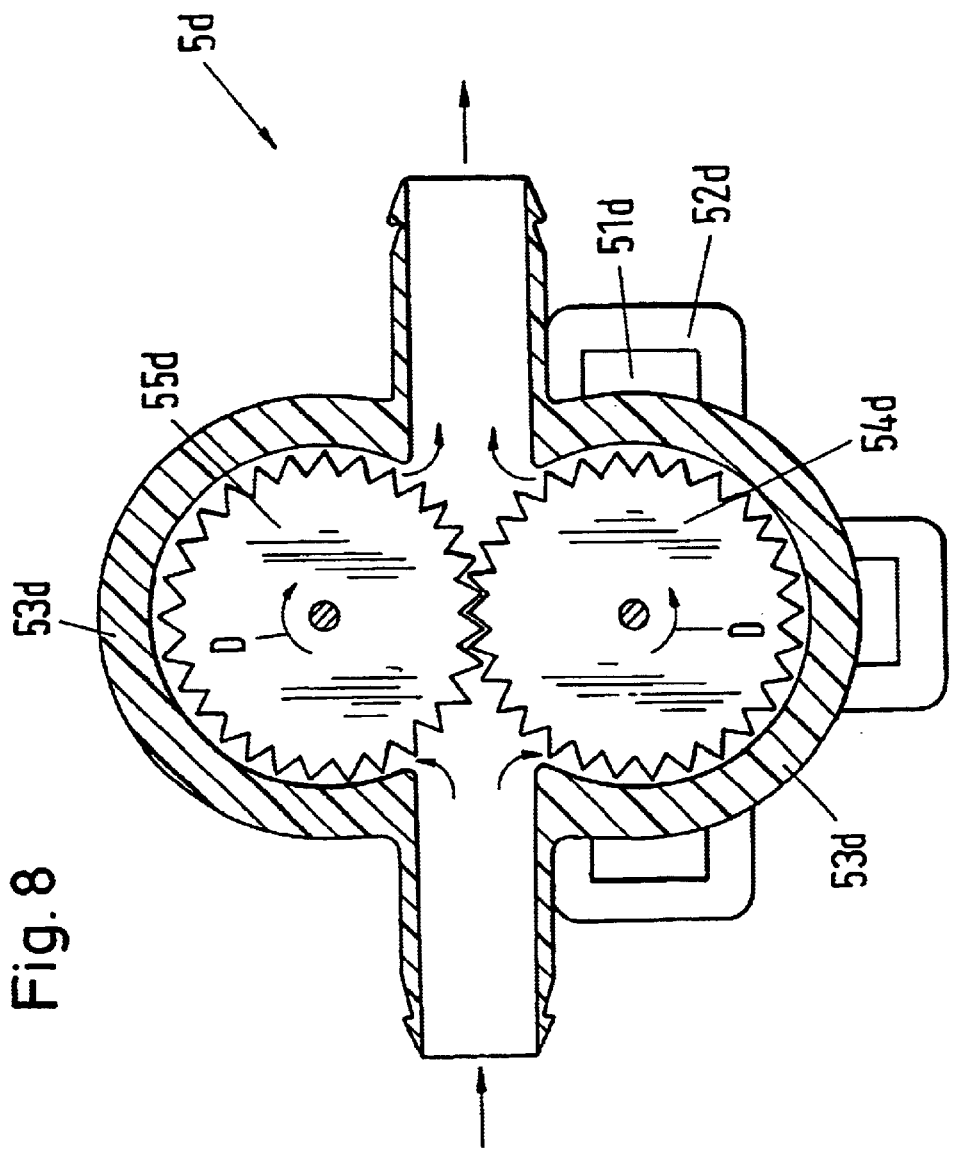
FIG. 8 shows the gear pump of FIG. 6 and is taken along line VIII—VIII in FIG. 6.

In FIG. 8 one recognizes a view of the gear pump 5d in accordance with line VIII—VIII in FIG. 6, from which the principle of functioning of the gear pump becomes clear. The direction of rotation of the gears is indicated through the arrows D, with only the gear 54d being motor-driven and the gear 55d being driven through the engaging of the teeth of the gears 54d and 55d into one another. The nutrient solution N is conveyed in the manner which can be recognized through the corresponding arrows in FIG. 8. Because practically only a very small cavity arises in the region in which the teeth of the two gears 54d and 55d engage into one another, the nutrient solution is practically conveyed between the respective gear 54d or 55d respectively and the pump housing 53d.

Figure 7:
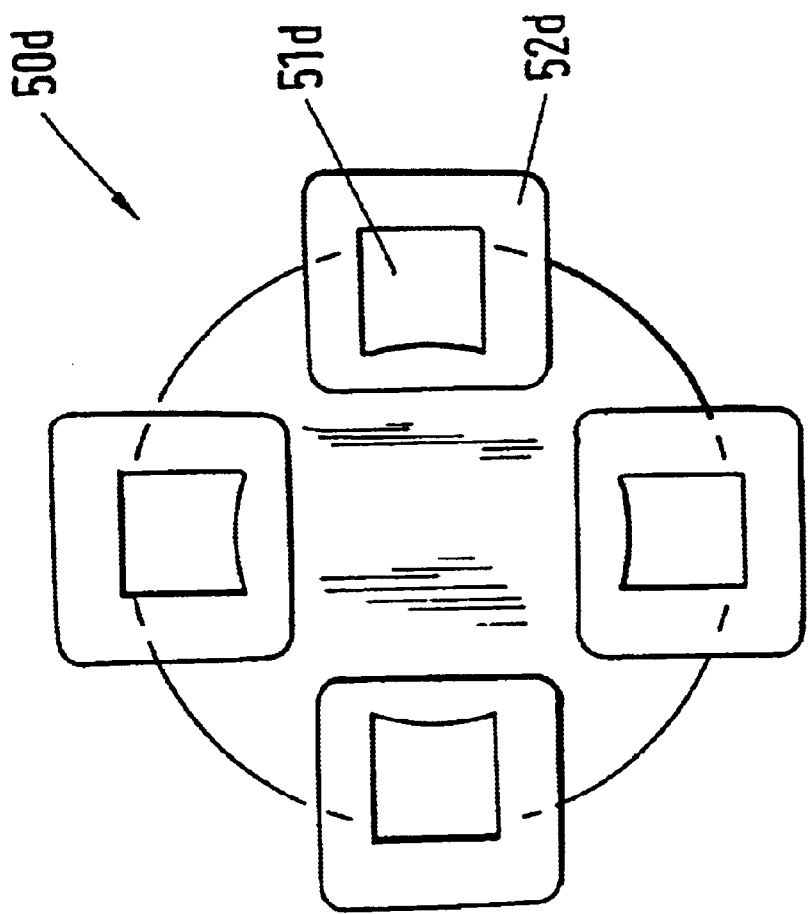
FIG. 7 shows the stator of the expendable pump of FIG. 6 in a view from above.

It is self-evident that the expendable pump which was explained with reference to FIG. 6, FIG. 7 and FIG. 8 need not necessarily be designed as a gear pump, but can of course also be designed as a centrifugal pump or as a pump of another type.

In FIG. 9 a further exemplary embodiment of a bioreactor in accordance with the invention is illustrated in which the reaction container 1e comprises a flexible pouch, for example a foil pouch 10e, which is received in a reception which is dimensionally stable and which can for example be designed as a thermal jacket 100e. The thermal jacket 100e imparts the required stability to the foil pouch 10e and keeps the pouch contents at a desired temperature. Furthermore, one recognizes a gas outlet 11e and a supply line 2e for the nutrient solution N. The nutrient solution N has already previously been mixed with oxygen or freed from carbon dioxide respectively with the help of an oxygenator 3e. Where appropriate a reservoir (not illustrated) with nutrient solution N can also be provided, out of which the nutrient solution is conveyed with the help of the expendable pump 5e or a pump 5e with expendable parts respectively.

A semi-permeable membrane 101e which is permeable for the nutrient solution N but not however for the cells C which are arranged in the foil pouch can be provided in the foil pouch 10e. Through this, sensitive cells are not exposed to the relatively large shear forces in the pump or in the oxygenator respectively. In order that the semi-permeable membrane 101e cannot become clogged, the flow direction of the nutrient solution can be reversed now and then. On the other hand the membrane 101e could also be arranged vertically. The space in which the cells C are located can also be filled with "microcarriers", in order to be able to cultivate cells which require an anchoring (so-called "anchorage dependent cells").

FIG. 10 shows finally an exemplary embodiment of how the inlet of the reaction container can be designed. If the inlet is designed as is shown in FIG. 10, then an oxygenator (involving more expense) can be dispensed with and a gaseous medium, for example oxygen, can be admixed to the nutrient solution N in accordance with the Venturi principle. In this case a pump for the supplying of the gaseous medium could be dispensed with. Of course, the gas supply can also take place separately in the known manner, e.g. by means of a membrane pump which is provided for this purpose. The solution with a separate membrane pump for the gas supply involves admittedly more expense, but also permits in return a better setting of the gas supply which is above all independent of the nutrient solution supply.

In FIG. 10 one therefore recognizes the end 2f of the supply line, which opens in an attachment piece 100f into the foil pouch 10f. But a passage 101f, through which the gaseous medium, e.g. oxygen, can then be admixed to the nutrient solution during the supplying of the nutrient solution N, also opens into the attachment piece.

Finally, it should also be noted that in all explained exemplary embodiments not only the pump or parts thereof, but also all other constituents of the bioreactor which come into contact with the medium, can be designed as expendable parts. In particular the reactors can also be delivered already assembled and packed in a sterile condition, so that no danger of contamination exists, since the parts which are exposed to the danger of contamination are all replaced after a single use.

Figure 11:
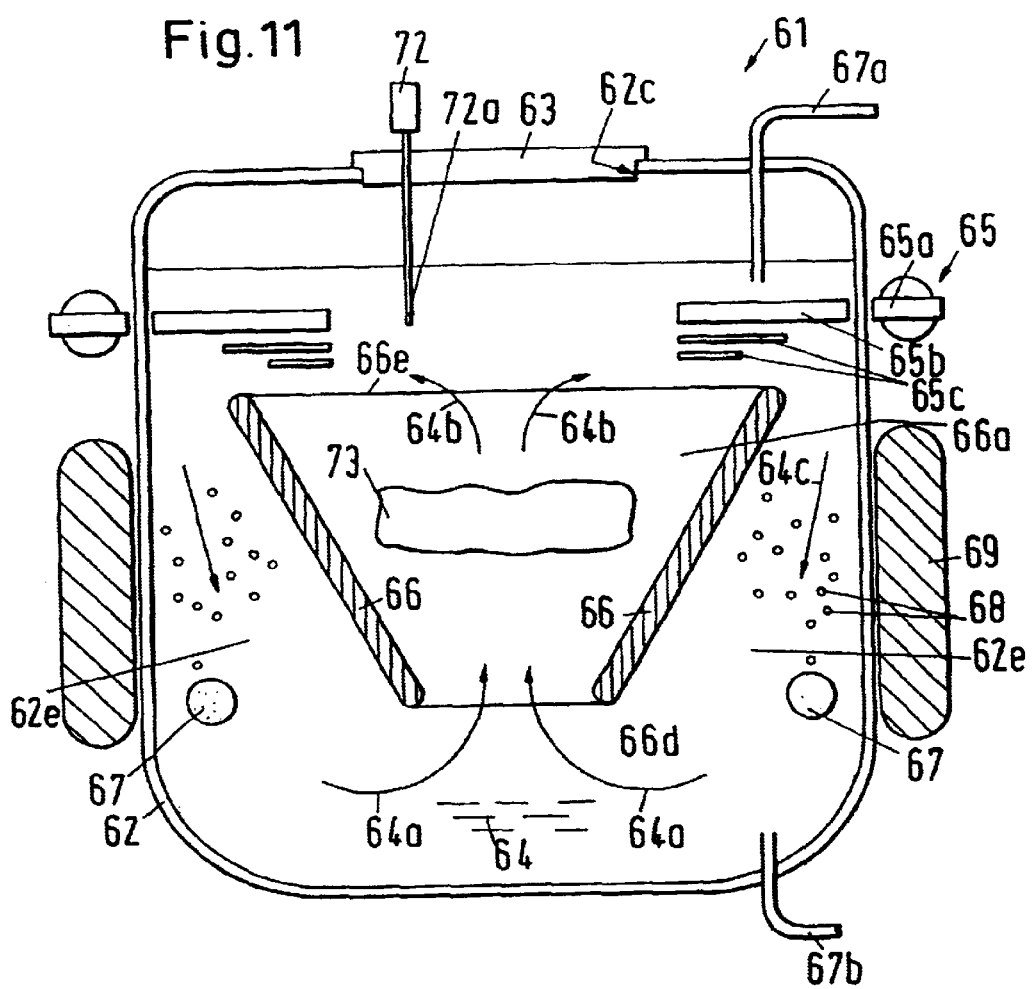
FIG. 11 is a longitudinal section through a first bioreactor.

The bioreactor 61 which is illustrated in FIG. 11 comprises a container 62 which has an opening 62c above, which can be closed by a closure 63. Arranged in the inner space of the container 62 is a flow guiding means 66 having the shape of a truncated cone which is formed as a hollow body, the cross-sectional area of which increases upwardly. The inner space of the container 62 is largely filled with a liquid 64, which is set into a circulation flow by the vaned wheel 65c of the motor 65, so that the liquid 64 has the flow direction which is illustrated by the arrows 64a, 64b, 64c. The liquid which flows in the direction of the arrows 64a enters from below with relatively high flow speed via the entry opening 66d into the inner space 66a of the flow guiding means 66, flows upwards in the inner space 66a with decreasing speed, and leaves the inner space 66a above again with relatively low flow speed through the outlet opening 66e, as illustrated by the arrows 64b. In the inner space 66a the flow speed decreases as a result of the upwardly widening cross-section. The inner space 66a forms the first flow chamber. If the diameter of the outlet surface 66e is for example twice as large as the diameter of the inlet surface 66d, then the speed at the outlet surface 66e corresponds to one-fourth of the speed at the inlet surface 66d. The buoyancy force which is caused by the flow speed still amounts at the outlet surface 66e to one-sixteenth of that at the inlet surface 66d. The substance 73, which is arranged in the inner space 66a, is held in an equilibrium position through the upwardly flowing liquid, with the flotation height or the equilibrium position respectively of buoyancy force and gravitation setting in by itself as a result of the weight and the working surface of the substance.

Arranged above the flow guiding means 66 is a pump 65, which comprises an iron stator 65a which is arranged outside the container 62 and a rotor 65b which is arranged within the container 62. A vaned wheel 65c is firmly connected to the rotor 65b. An apparatus of this kind comprising a stator and a rotor which is held and driven by magnetically acting forces is also designated as a bearingless motor and is known to the skilled person, for example from the specification WO 96/31934.

The vaned wheel 65c produces the circular flow which is illustrated with the arrows 64a, 64b, 64c. Formed between the container 62 and the flow guiding means 66 is an inner space 62e, also designated as second flow chamber, having a cross-sectional area which widens downwardly. This has the result that the liquid which flows downwardly in the flow direction 64c has a flow speed which decreases downwardly.

Arranged below in the inner space 66e is a ring-shaped distributor 67, through which air or oxygen is led in for the gas flushing of the liquid 64, which forms air bubbles 68 within the liquid 64 which have the tendency to rise. Through the liquid, which flows downwardly in the direction 64c, the rising of the air bubbles 68 is delayed or prevented, which furthers the gas exchange to the liquid 64.

The container 62 is surrounded on the outside by a ring-shaped heating apparatus 69. The inner space of the container 62 is supplied via an inlet line 67a and an outlet line 67b with a nutrient liquid. A measurement probe 72 with probe head 72a enables for example a monitoring of the pH value or the temperature of the liquid 64.

The bioreactor 61 which is illustrated in FIG. 11 has the advantage that the substance 73 is easily accessible via a closure 63 having a large diameter.

Figure 11A:
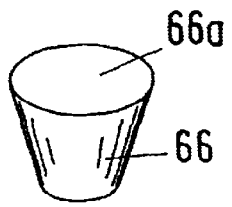
FIG. 11a is a perspective detailed view of the flow guiding means.

FIG. 11a shows a perspective illustration of the flow guiding means 66 with inner space 66a.

Figures 12A, 12B, 13A:
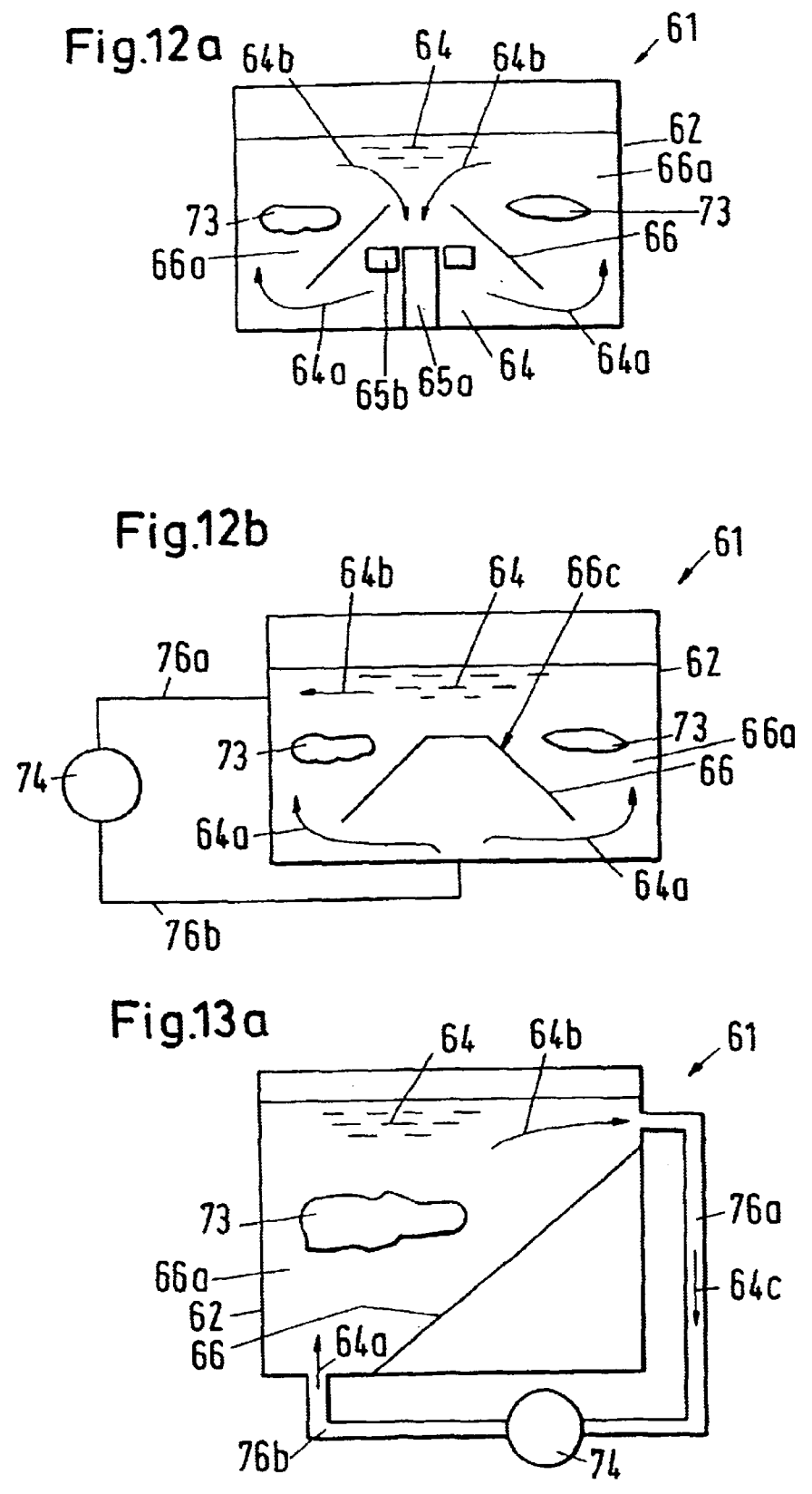

FIG. 12a shows schematically a longitudinal section through a further exemplary embodiment of a bioreactor 61, which differs with respect to the example which is illustrated in FIG. 11 in that the flow guiding means 66 is arranged in reverse, which means with a downwardly widening cross-section. The pump 65 comprising the iron stator 65a and the rotatable part 65b with vaned wheel 65c causes a flow in the direction 64a, 64b in the liquid 64. The inner space 66a, in which the liquid flows upwards, and in which the substance 73 is held, is located between the flow guiding means 66 and the outer wall of the container 62.

FIG. 12b shows schematically a longitudinal section through a further exemplary embodiment of a bioreactor 61, which differs with respect to the example which is illustrated in FIG. 12a in that the flow guiding means 66 is designed to be tight above and that the fluid pump 74 is arranged outside the container 62, with the pump 74 being connected in a fluid conducting manner to the inner space of the container 62 via lines 76a, 76b. The fluid which flows in the direction 64a enters from below into the inner space 66a and flows around the substance 73.

FIG. 13a shows schematically a longitudinal section through a further exemplary embodiment of a bioreactor 61, which likewise has a fluid pump 74 which is arranged outside the container 62 and which is connected to the inner space in a fluid conducting manner via lines 76a, 76b. The flow guiding means 66 is designed to be upwardly widening only on the one inner side of the container 62. The substance 73 is held in flotation through the liquid which circulates in the direction 64a, 64b, 64c in the inner space 66a.

Figure 13C:
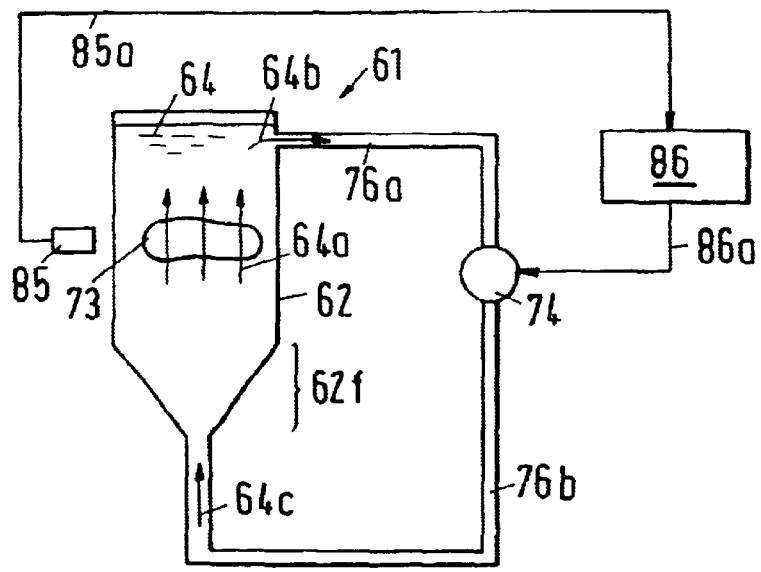
Figure 13B:
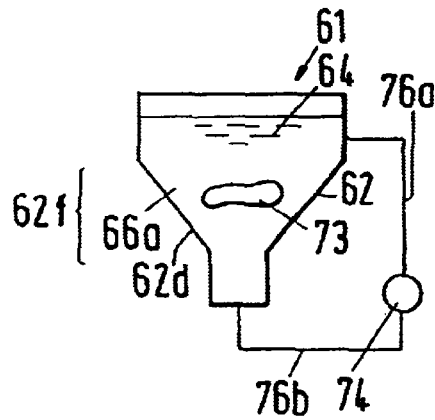

FIG. 13b shows schematically a longitudinal section through a further exemplary embodiment of a bioreactor 61, which likewise has a fluid pump 74 which is arranged outside the container 62 and which is connected to the inner space in a fluid conducting manner via lines 76a, 76b. Along a section 62f the container 62 has an upwardly widening container wall 62d. Along this section 62f a flow develops with a flow speed which decreases upwardly, so that the inner space 66a is formed for the holding in flotation of the substance 73 along this section 62f.

FIG. 13c shows schematically a longitudinal section through a further exemplary embodiment of a bioreactor 61, which likewise has a fluid pump 74 which is arranged outside the container 62 and which is connected to the inner space in a fluid conducting manner via lines 76a, 76b. The line 76a opens into the container 62 in a section 62f which widens upwardly. A cylindrically designed container section 62 is arranged afterwards, within which a linear flow 64a develops and within which the substance 73 is arranged. The height position of the substance 73 is monitored by a sensor 85. A regulation apparatus 86 is connected in a signal conducting manner via an electrical line 85a, 86a to the sensor 85 and to the pump 74. The speed of rotation of the pump 74 is regulated in such a manner that the substance 73 remains in the region of the sensor 85.

Figure 13D:
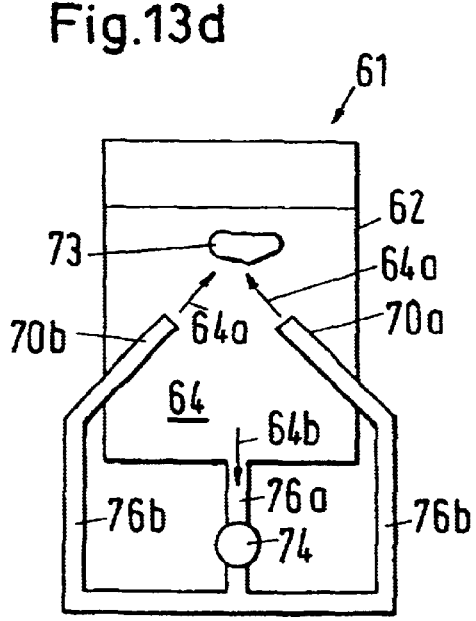

FIG. 13d shows schematically a longitudinal section through a further exemplary embodiment of a bioreactor 6 1, which likewise has a fluid pump 74 which is arranged outside the container 62 and which is connected in a fluid conducting manner via lines 76a, 76b to the inner space. A plurality of, for example three, nozzles 70a, 70b open inside the container 62 with orientation onto the substance 73, with the flow direction which is illustrated by 64a having a flow speed which is reduced upwardly, so that the substance 73 is supported by this flow and automatically finds an equilibrium position.

In all bioreactors 61 which are illustrated in FIGS. 11 to 13*d* the substance 73 is held in a state of flotation by means of the same method, namely in that the substance 73 is acted upon with a fluid, the flow of which acts counter to the gravitation acting on the substance 73 in such a manner that the substance 73 is held in flotation. In the exemplary embodiments in accordance with FIGS. 11, 12*a*, 12*b*, 13*a*, 13*b* and 13*d* the fluid has a lower flow speed in the inner space 66*a* with increasing height. In the exemplary embodiment in accordance with FIG. 13*c* the speed of the fluid is regulated with a sensor 85 in dependence on the position of the substance 73.

In the exemplary embodiment in accordance with FIG. 11 a downwardly flowing flow 64*c* is produced within the container 62, with a gaseous fluid such as air or oxygen being led in into this flow 64*c*. The flow speed of the flow 64*c* can be chosen in such a manner that the gaseous fluid which is input is slowed down or even no longer rises in the container 62.

Figure 15:
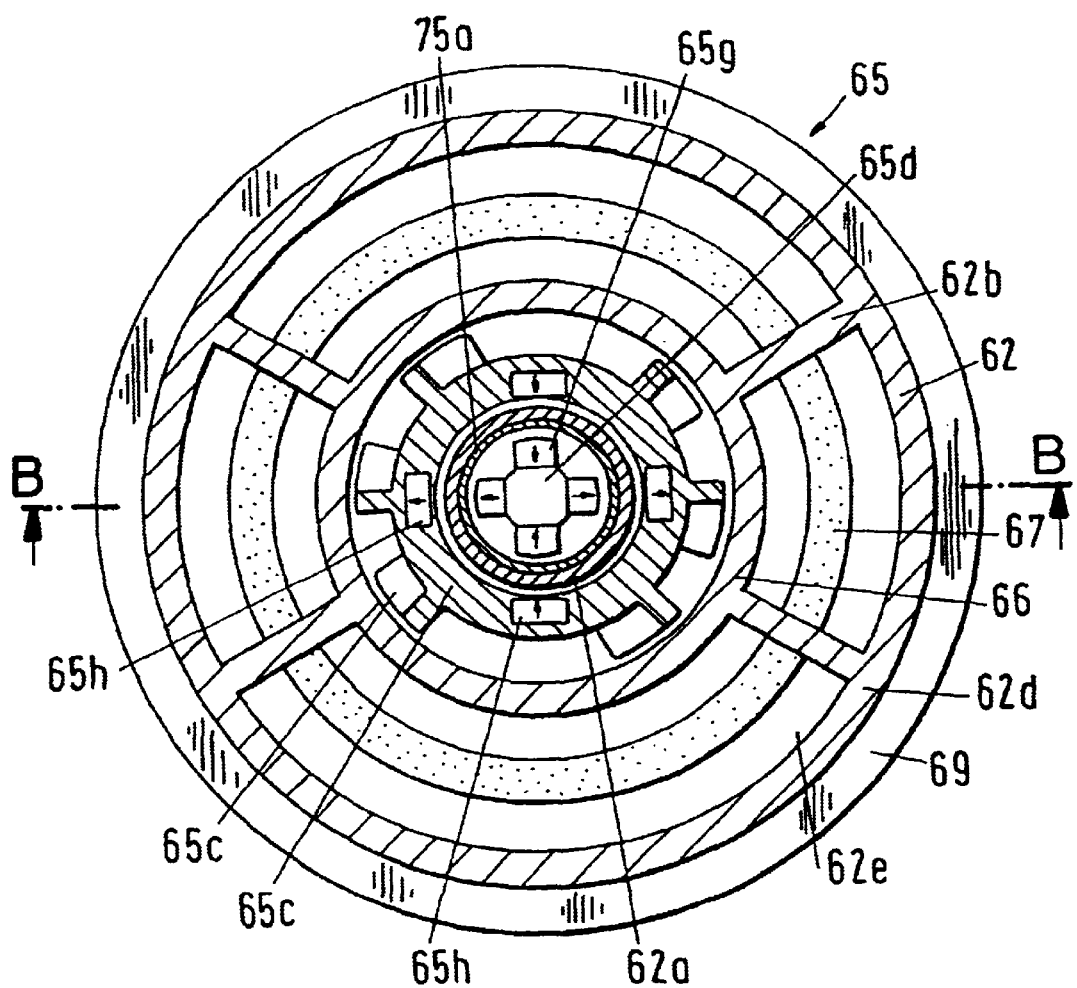
FIG. 15 is a section taken along line A—A of FIG. 14.

FIG. 14 shows with a longitudinal section along line B—B in accordance with FIG. 15 a further exemplary embodiment of a bioreactor 61. Otherwise designed similarly as the bioreactor 61 which is illustrated in FIG. 11, in the bioreactor 61 in accordance with FIG. 14, the pump 65 is arranged below in the region of the entry opening 66*d* of the flow guiding means 66. A vaned wheel 65*c* is rotatably arranged within the container 62 on a step bearing 65*i*, with the step bearing 65*i* lying on the container wall 62*d*. A plurality of permanent magnets 65*h* which are arranged over the periphery is cast in within the vaned wheel 65*c*, which consists of a plastic. Arranged outside the container 62 is a magnetic coupling which is journalled so as to be rotatable in the direction 65*e* and which comprises two bearings 65*f* and a ring-shaped permanent magnet 65*g*. The rotatable shaft 65*d* is driven by a non-illustrated motor. A stand apparatus 75 forms a gap pot 75*a* which is designed to be cylindrical and which is arranged to extend between the two permanent magnets 65*g*, 65*h*. The container wall 62*d* forms at the gap pot 75*a* a gap pot section 62*a*. The magnetic coupling, which comprises the permanent magnets 65*h*, 65*i*, causes the rotational motion of the rotatable shaft 65*d* to be transmitted to the vaned wheel 65*c* and the vaned wheel 65*c* to be held with respect to a tilting. The vaned wheel 65*c* is thus passively magnetically held.

The container 62 and the vaned wheel 65*c* which is rotatably journalled therein are preferably designed for a single use as an expendable product. The container 62 can be placed onto the heating apparatus 69 as well as onto the gap pot 75*a*, so that the container 62 is held securely and the vaned wheel 65*c* can be driven via the rotatably journalled magnetic coupling.

The container 62 can, as illustrated in FIG. 14, have additional openings 63*a*, 63*b*, for example for measurement probes.

FIG. 15 shows a cross-section along line A—A in accordance with FIG. 14. Arranged in the center is the rotatable shaft 65*d* at which four permanent magnets 65*g* which are arranged with spacing are secured. The container 62 forms with its container wall 62*d* a gap pot section 62*a*. The gap pot 75*a* is arranged between the gap pot section 62*a* and the rotatable shaft 65*d* with permanent magnet 65*g*. The gap pot section 62*a* is surrounded by the vaned wheel 65*c*, within which four permanent magnets 65*h* are arranged, with their polarization, illustrated by arrows, being oriented to be matched to that of the permanent magnets 65*g*. The flow guiding means 66 is connected via fluid guiding parts 62*d* to the outer wall of the container 62. The flow chamber 62*e*, which widens downwardly, is arranged between the flow guiding means 66 and the outer wall of the container 62. In addition the distributor 67, which is designed to be ring-shaped, is shown.

Figure 16:
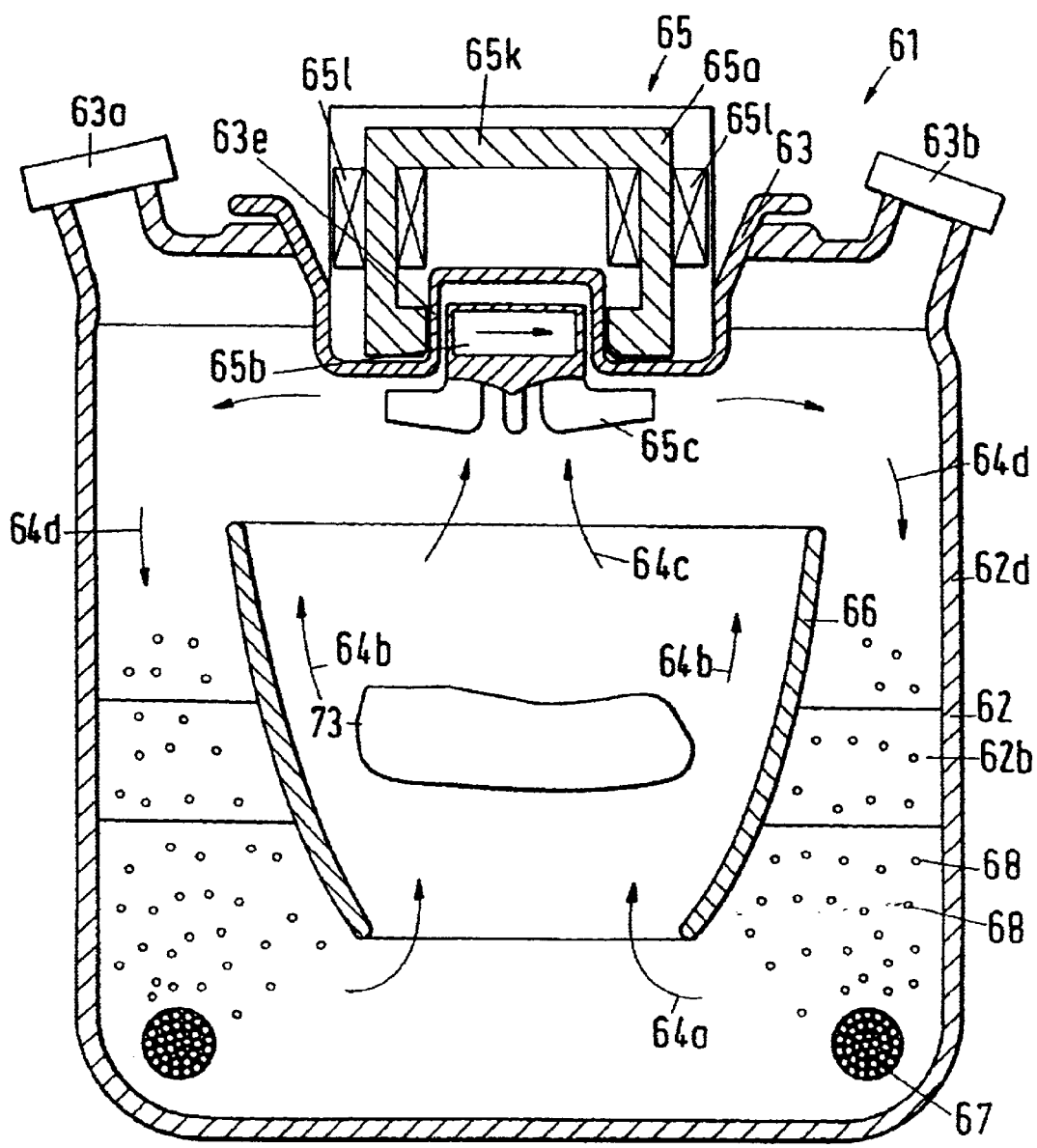
FIG. 16 is a longitudinal section through a further bioreactor with a vaned wheel which is arranged at the closeable opening.

FIG. 16 shows a longitudinal section through a further exemplary embodiment of a bioreactor 61. In contrast with the bioreactor 61 which is illustrated in FIG. 11, in the bioreactor 61 in accordance with FIG. 16 the pump 65 is arranged in the closure 63 and is designed as a centrifugal pump. The pump 65 is designed as a split tube motor and comprises the firmly arranged iron stator 65*a* and the contactlessly rotatably journalled, rotatable part 65*b*, which is designed as a permanent magnet and which is firmly connected to the vaned wheel 65*c*. The iron stator 65*a* comprises a soft iron 65*k* which is surrounded by a plurality of coils 65*l*. The coils 65*l* are arranged and can be excited in such a manner that the rotatable part 65*b* is driven and held without contact. The closure 63 has a gap pot section 63*e*, which is arranged in the gap between the iron stator 65*a* and the permanent magnet 65*b*.

An arrangement of this kind comprising a stator and a rotor which is held and driven with magnetically acting forces is also designated as a temple motor and is known to the skilled person, for example from the specification WO 96/31934, in particular from its FIG. 12.

The flow guiding means 66 is firmly connected via fluid guiding parts 62*b* to the container wall 62*d*. The flow guiding means 66 has a cross-section which widens upwardly in the manner of a belly. The flow guiding means 66 can be designed in a plurality of further embodiments in such a manner that an upwardly enlarging cross-sectional area results.

Figure 17:
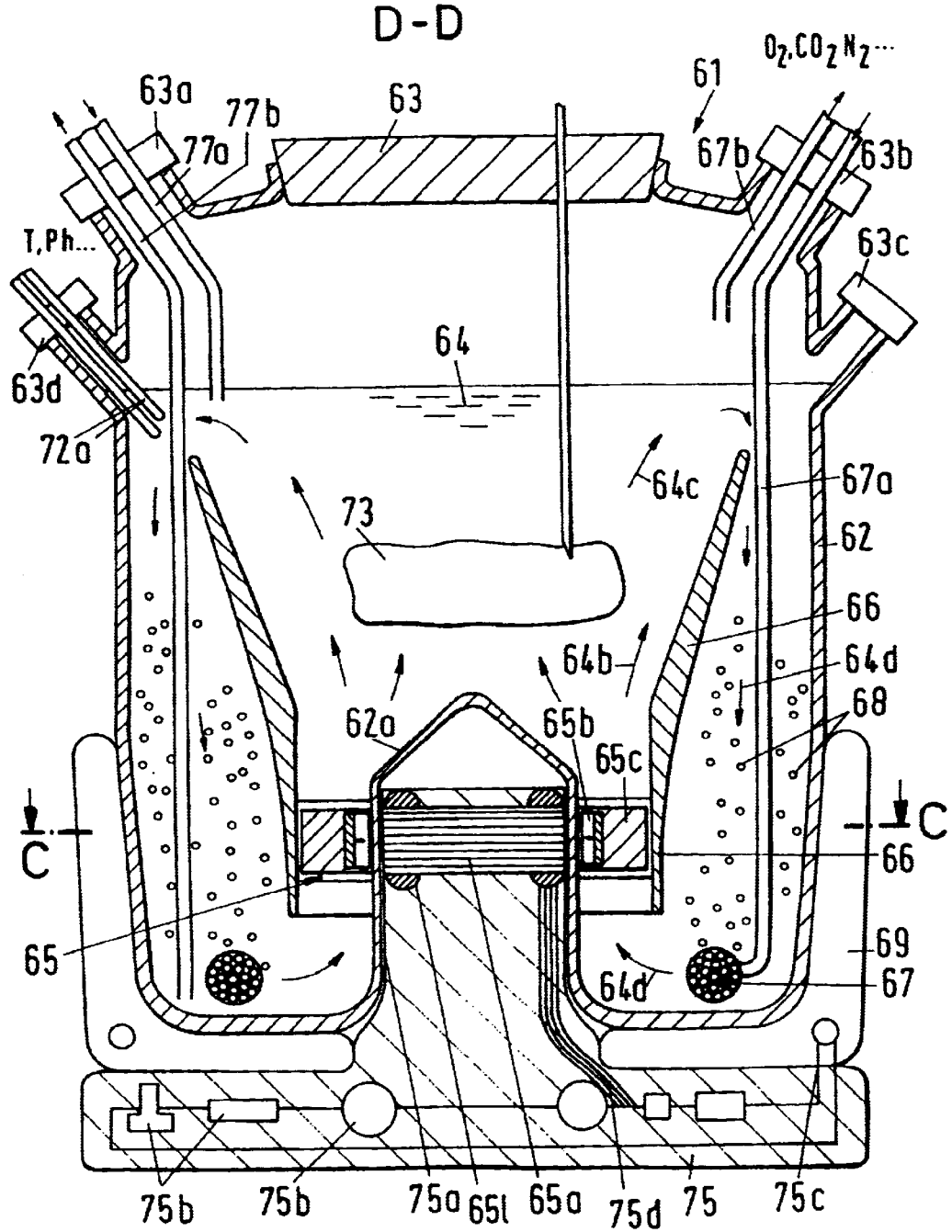
FIG. 17 is a longitudinal section along line D—D through a further bioreactor with a magnetically coupled vaned wheel.
Figure 18:
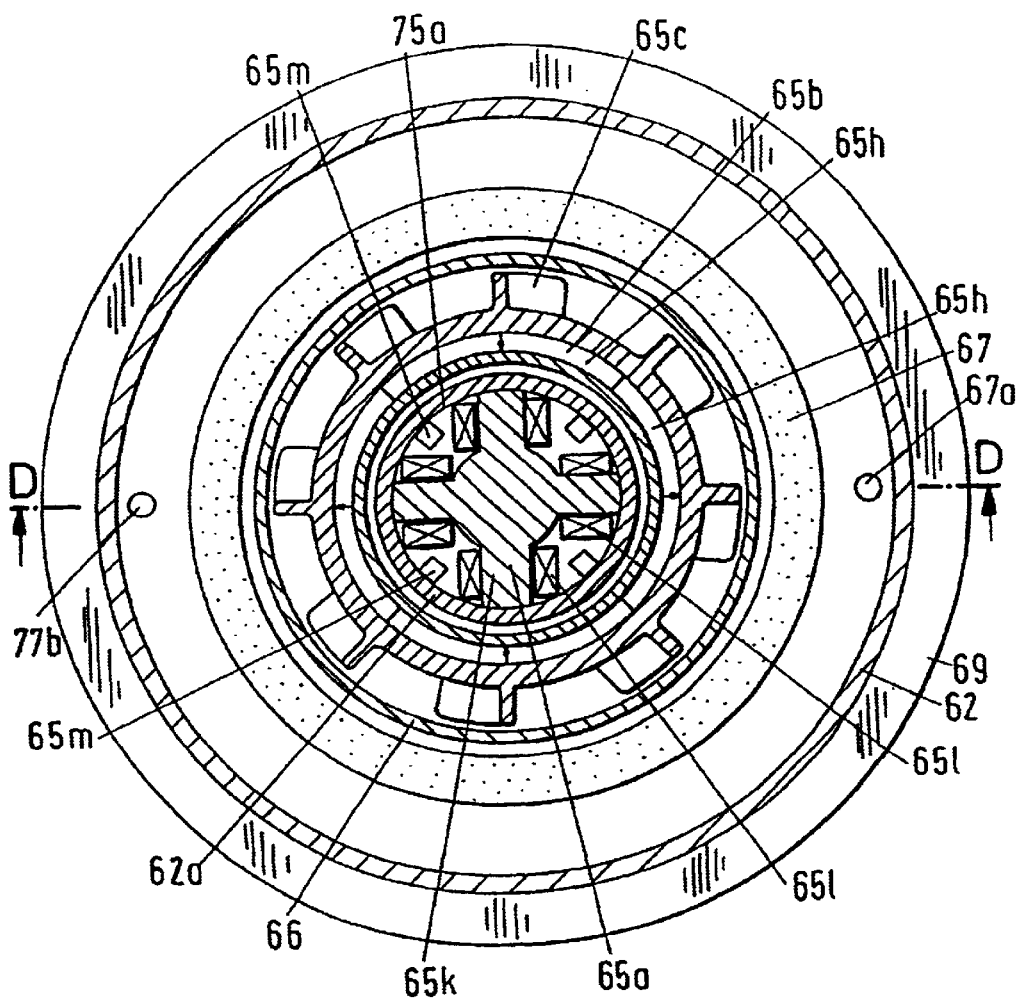
FIG. 18 is a section taken along line C—C of FIG. 17.

With a longitudinal section along line D—D in accordance with FIG. 18, FIG. 17 shows a further exemplary embodiment of a bioreactor 61. In contrast with the bioreactor 61 which is illustrated in FIG. 14 the pump 65 has a completely magnetically journalled and driven rotatable part 65*b* with vaned wheel 65*c*. The bearingless drive of the pump 65 is illustrated in detail in cross-section along the section line C—C which is illustrated in FIG. 18. The method of functioning of a drive of this kind is for example disclosed in the specification WO 98/59406. The iron stator 65*a* is designed as a cross-shaped sheet metal package 65*k*, at the arms of which coils 65*l* are arranged. Through a corresponding excitation of the coils 65*l* a rotating magnetic field can thereby be produced. The rotatable part 65*b* comprises four permanent magnets 65*h* which are arranged in the peripheral direction, with two adjacent permanent magnets 65*h* in each case being polarized in opposite directions. These permanent magnets 65*h* are cast in or encapsulated in the vaned wheel 65*c* or in the pump blades 65*c* respectively. Sensors 65*m* are arranged in the stator which measure the position of the permanent magnets 65*h*. Electronic components 75*b* are arranged in the stand apparatus 75', comprising an electrical lead 75*d* for the coils 65*l* of the motor and with an electrical lead 75*c* for the heater 69. In addition electrical lines are provided which connect the sensors 65*m* to the electronic components 75*b*. The coils 65*l* are excited in such a manner that the rotatable part 65 with pump blades 65*c* is held and driven without contact. The pump 65 forms an axial pump. The gap pot 75*a* and the gap pot section 62*a* of the container wall 62*d* are arranged between the iron stator 65*a* and the rotatable part 65*b*.

The stand apparatus 75 and the heater 69 form a firm support and holder into which the container 62 can be introduced. This arrangement has the advantage that the container 62 can be placed very simply onto the stand apparatus 75 with the heater 69, End the axial pump 65 can subsequently be operated immediately without the need for additional manipulations. The container 62 with rotatable part 65b and pump blades 65c is designed as an expendable product, whereas the expensive components of the stand apparatus 75 and the heater 69 can be used as often as desired. In addition the stand apparatus 75 and the heater 69 need not be sterile, so that no laborious cleaning process is required. Advantages of this arrangement are the facts that the inner space of the container 62 can be kept sterile without problem, that the container 62 can be manufactured economically and that the stand apparatus 75 can be operated without a laborious cleaning process and thus economically.

In the container 62 in accordance with FIG. 17 the inlet and outlet lines 67a, 67b for gases such as $O_2$, $CO_2$, $N_2$ pass through the closure 63b, with the inlet line 67a being connected in a fluid conducting manner to the ring-shaped distributor 67. The inlet and outlet lines 77a, 77b for the nutrient medium pass through the closure 63a. In addition, probes with probe heads 72a, for example for the measurement of temperature or pH value, pass through the closure 63d.

Figure 19:
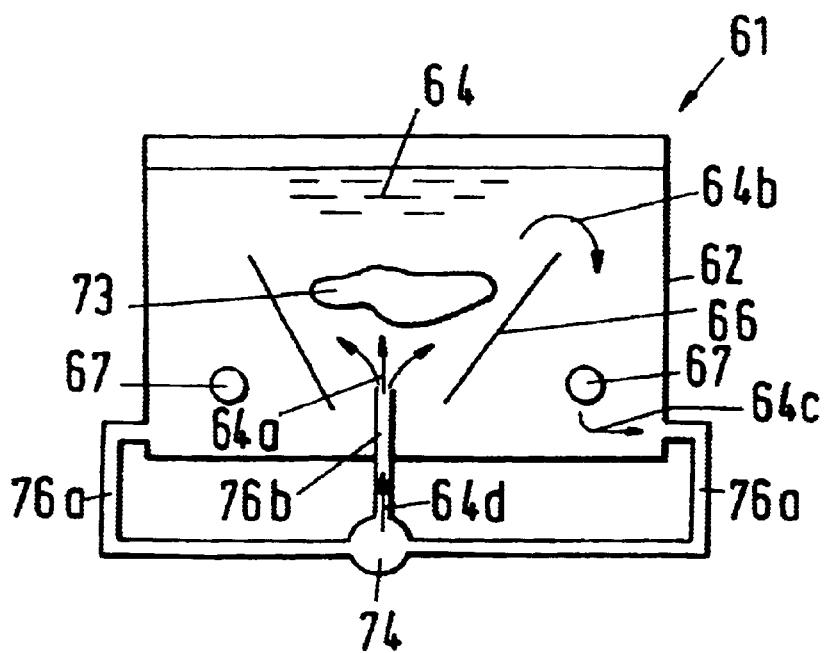
FIG. 19 is a longitudinal section through a further bioreactor.

FIG. 19 shows schematically a longitudinal section through a further exemplary embodiment of a bioreactor 61, which likewise has a fluid pump 74 which is arranged outside the container 62 and which is connected in a fluid conducting manner to the inner space via lines 76a, 76b. The line. 76b opens into the section of the flow guiding means 66 which widens upwardly. The fluid is conducted to the fluid pump 74 via the lines 76a which are arranged in the base region of the container 62, so that the fluid has the flow behavior which is indicated by the arrows 64a, 64b, 64c.

What is claimed is:

1. Bioreactor comprising a reaction container for a substance to be acted upon with a medium, and a pump for conveying the medium, the pump including a pump wheel arranged in the reaction container and a separate drive stator into which the reaction container together with the pump wheel which is arranged therein can be inserted.

2. Bioreactor in accordance with claim 1 wherein at least one of the pump, the pump wheel and the reaction container are manufactured of a plastic.

3. Bioreactor in accordance with claim 1 including permanent magnets arranged in the pump wheel.

4. Bioreactor in accordance with claim 1 wherein the bioreactor is a hollow fiber bioreactor.

5. Bioreactor in accordance with claim 1 wherein the bioreactor comprises an airlift reactor.

6. Bioreactor in accordance with claim 1 wherein, in addition to the pump or the parts of the pump, all other constituents of the bioreactor which come into contact with the medium comprise single use parts.

7. Bioreactor in accordance with claim 1 wherein at least one of the pump, the pump wheel and the reaction container comprises single use parts.

8. Bioreactor comprising a reaction container forming an airlift reactor for a substance to be acted upon with a medium, and a pump for conveying the medium comprising at least one of a pump for single use and single use parts for the pump, in which reaction container a hollow body is arranged which has a jacket connected at its lower end to a wall of the reaction container that tapers in the direction towards an upper end of the reaction container so that it subdivides an inner space of the reaction container into an upper chamber and a lower chamber, the upper and lower ends of the reaction container including respective upper and lower end surfaces of the hollow body which are liquid and gas permeable and enclose a cavity in which the substance to be acted upon can be arranged, a supply line for the liquid medium opening into the upper chamber and a suction device for a liquid medium and a supply device for a gaseous medium being provided in the lower chamber.

9. Bioreactor in accordance with claim 8 wherein the reaction container is cylindrical and the hollow body has the shape of a truncated circular cone; wherein the supply line opens into a ring-shaped distributor which is arranged in the upper chamber and surrounds the hollow body; and wherein the suction device for the liquid medium is arranged in the lower chamber and ring-shaped.

10. Bioreactor comprising a reaction container forming an airlift reactor for a substance to be acted upon with a medium, and a pump for conveying the medium comprising at least one of a pump for single use and single use parts for the pump, the bioreactor including a hollow body arranged in the reaction chamber of the airlift reactor, the hollow body including a jacket connected at its upper end to a wall of the reaction container and tapering in a direction towards a lower end of the reaction container so that it subdivides the inner space of the reaction container into an upper chamber and a lower chamber, the upper and lower ends of the reaction container including respective upper and lower end surfaces of the hollow body which are liquid and gas permeable and enclose a cavity in which the substance to be acted upon can be arranged, a supply line for the medium opening into the lower chamber, the medium being a mixture of a gaseous medium and a liquid medium; and a suction device for the medium in the upper chamber.

11. Bioreactor comprising a reaction container for a substance to be acted upon with a medium, and a pump for conveying the medium, the pump having a pump housing, a pump wheel arranged therein, and a separate drive stator, the pump housing together with the pump wheel being inserted in the drive stator.

12. Bioreactor according to claim 11 wherein the reaction container comprises a flexible pouch insertable into a dimensionally stable reception.

13. Bioreactor in accordance with claim 11 wherein at least one of the pump, the pump housing, the pump wheel and the reaction container comprises single use parts.

14. Bioreactor in accordance with claim 11 wherein at least one of the pump, the pump housing, the pump wheel and the reaction container are made of a plastic.

15. Bioreactor in accordance with claim 11 including permanent magnets arranged in the pump wheel.

16. Bioreactor in accordance with claim 11 wherein the bioreactor comprises an airlift reactor.

17. Bioreactor in accordance with claim 11 wherein the disposable pump is a gear pump.

* * * * *